US008911750B2

(12) United States Patent
Tsai et al.

(10) Patent No.: US 8,911,750 B2
(45) Date of Patent: Dec. 16, 2014

(54) LUNG VOLUME REDUCTION THERAPY USING CROSSLINKED BIOPOLYMERS

(76) Inventors: Larry W. Tsai, Boston, MA (US); Edward P. Ingenito, North Quincy, MA (US)

(*) Notice: Subject to any disclaimer, the term of this patent is extended or adjusted under 35 U.S.C. 154(b) by 1267 days.

(21) Appl. No.: 12/062,189

(22) Filed: Apr. 3, 2008

(65) Prior Publication Data

US 2008/0261884 A1 Oct. 23, 2008

Related U.S. Application Data

(60) Provisional application No. 60/909,806, filed on Apr. 3, 2007.

(51) Int. Cl.
*A61K 9/00* (2006.01)
(52) U.S. Cl.
USPC .......................... 424/400; 606/192; 424/78.17
(58) Field of Classification Search
None
See application file for complete search history.

(56) References Cited

U.S. PATENT DOCUMENTS

| | | | |
|---|---|---|---|
| 5,385,606 A | 1/1995 | Kowanko | |
| 5,583,114 A | 12/1996 | Barrows et al. | |
| 5,986,168 A * | 11/1999 | Noishiki | 424/422 |
| 6,033,654 A * | 3/2000 | Stedronsky et al. | 424/78.02 |
| 6,165,488 A | 12/2000 | Tardy et al. | |
| 6,458,889 B1 | 10/2002 | Trollsas et al. | |
| 6,585,639 B1 * | 7/2003 | Kotmel et al. | 600/116 |
| 6,610,043 B1 | 8/2003 | Ingenito | |
| 6,682,520 B2 | 1/2004 | Ingenito | |
| 6,709,401 B2 | 3/2004 | Perkins et al. | |
| 6,730,299 B1 | 5/2004 | Tayot et al. | |
| 6,878,141 B1 | 4/2005 | Perkins et al. | |
| 7,057,019 B2 | 6/2006 | Pathak | |
| 7,100,616 B2 | 9/2006 | Springmeyer | |
| 7,129,210 B2 | 10/2006 | Lowinger et al. | |
| 2002/0147462 A1 | 10/2002 | Mair et al. | |
| 2004/0047855 A1 | 3/2004 | Ingenito | |
| 2004/0131582 A1 | 7/2004 | Grinstaff et al. | |
| 2005/0002893 A1 | 1/2005 | Goldmann | |
| 2005/0158364 A1 | 7/2005 | Yuksel et al. | |
| 2005/0163819 A1 | 7/2005 | Yuksel et al. | |
| 2005/0228115 A1 * | 10/2005 | Auguste et al. | 524/505 |
| 2005/0244401 A1 | 11/2005 | Ingenito | |
| 2005/0281801 A1 | 12/2005 | Gong et al. | |
| 2005/0281802 A1 | 12/2005 | Gong et al. | |
| 2005/0282748 A1 | 12/2005 | Gong et al. | |
| 2005/0288702 A1 * | 12/2005 | McGurk et al. | 606/192 |
| 2006/0249164 A1 | 11/2006 | Springmeyer | |
| 2007/0098675 A1 | 5/2007 | Elisseeff et al. | |

FOREIGN PATENT DOCUMENTS

| | | |
|---|---|---|
| EP | 1043034 A1 | 10/2000 |
| EP | 0650512 B1 | 10/2001 |
| WO | WO-94/01508 | 5/1994 |
| WO | WO-01/13908 A2 | 3/2001 |
| WO | WO-2006/066234 A2 | 6/2006 |
| WO | WO-2007/055950 A2 | 5/2007 |

OTHER PUBLICATIONS

Ingenito, E.P., et al.; "Bronchoscopic Lung Volume Reduction Using Tissue Engineering Principles," Am. J. Respir. Crit. Care Med. 2003, vol. 167, pp. 771-778.
Ingenito et al.; "Bronchoscopic Volume Reduction: A Safe and Effective Alternative to Surgical Therapy for Emphysema," *Am. J. Resp. Crit. Care Med.* 2001, vol. 164, pp. 295-301.
International Search Report for PCT/US2008/059263.
Ehrman, W. J. et al., "Transbronchial Catheter Directed Lung Volume Reduction Using Biologic Glue: Preliminary In Vitro Results", Abstract, Western Thoracic Surgical Association Meeting, The Big Island, Hawaii, Jun. 21-24, 2000.
Furst, W. et al., "Release of Glutaraldehyde From an Albumin-Glutaraldehyde Tissue Adhesive Causes Significant In Vitro and In Vivo Toxicity", *Ann. Thorac. Surg.*, 79:1522-9 (Elsevier, Inc., Vienna, Austria, 2005).
Huang-Lee, L. L. H. et al., "Biochemical change and cytotoxicity associated with the degreadation of polymeric glutaraldehyde derived crosslinks", *Journal of Biomedical Materials Research*, 24:1185-1201 (John Wiley & Sons, Inc., US, 1990).
Speer, D. P. et al., "Biological effects of residual glutaraldehyde in glutaraldehyde-tanned collagen biomaterials", *Journal of Biomedical Materials Research*, 24:753-764 (John Wiley & Sons, Inc., US, 1980).
Tansley, P. et al., "A prospective, randomized, controlled trial of the effectiveness of BioGlue in treating alveolar air leaks", *The Journal of Thoracic and Cardiovascular Surgery*, 132(1):105-112 (The American Association of Thoracic Surgery, USA, 2006).
Zeiger, E. et al., "Genetic toxicity and carcinogenicity studies of glutaraldehyde—a review", *Mutation Reseach*, 589:136-151 (Elsevier B.V. 2005).
Chao, H.-H. et al., "BioGlue: Albumin-Glutaraldehyde Sealant in Cardiac Surgery", *J. Card. Surg.*, 18(6):500-503 (USA, Nov. 1, 2003).
Kobayashi, H. et al., "In Vivo Evaluation of a New Sealant Material on a Rat Lung Air Leak Model", *Journal of Biomedical Materials Research*, 58(6):658-665 (John Wiley & Sons, USA, 2001).
Lai, M. et al., "Repair of Major Airway Injury Using Ablumin-Glutaraldehyde Glue", *ANZ J. Surg.*, 71:555-556 (Australia, 2001).

(Continued)

*Primary Examiner* — Nissa Westerberg
(74) *Attorney, Agent, or Firm* — Dana M. Gordon; Foley Hoag LLP

(57) ABSTRACT

One aspect of the present invention relates to bronchoscopic lung volume reduction using solutions of biopolymers that can be polymerized in situ with a crosslinker and a polymeric additive which accelerates the cross-linking reaction. In certain embodiments, the biopolymer solutions can be in the form of a foam or gel. The biopolymer compositions disclosed herein may also be used for indications other than lung volume reduction, such as sealing fistulas or performing emergency tamponade of vessels.

2 Claims, 9 Drawing Sheets

(56) References Cited

OTHER PUBLICATIONS

Passage, J. et al., "Bioglue: A Review of the Use of This New Surgical Adhesive in Thoracic Surgery", *ANZ J. Surg.*, 75:315-318 (Australia, 2005).

Potaris, K. et al., "Preliminary results with the use of an albumin-glutaraldehyde tissue adhesive in lung surgery", *Med. Sci. Monit.*, 9(7):P179-183 (Greece, 2003).

Supplementary European Search Report from corresponding European application EP 08745018.5 dated Dec. 18, 2012.

* cited by examiner

[A]
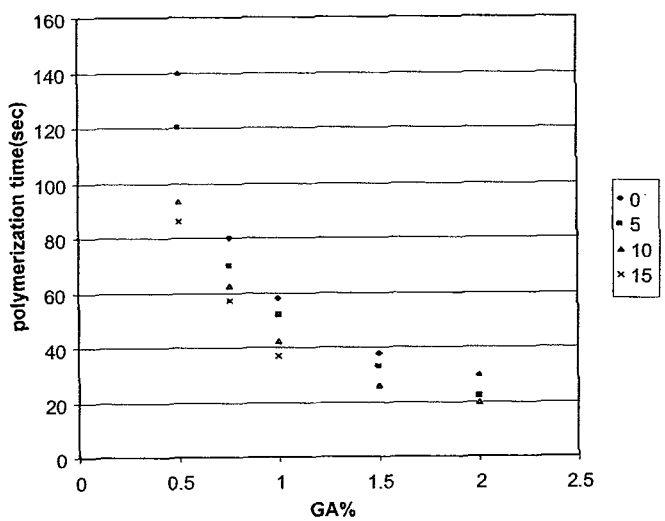
[B]
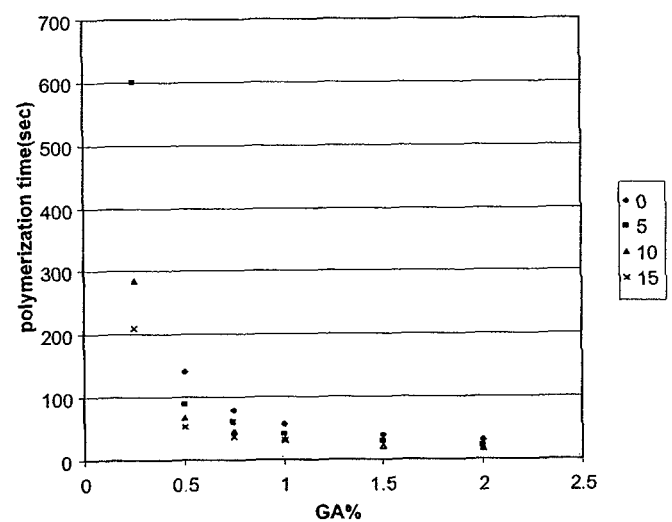
Figure 3

Figure 7

Table 1. Foamability of 22.5% HSA, 4.5% PVP

| Liquid (mL) | Air (mL) | Liquid:Air | Homogeneity | Unincorporated Air (mL) |
|---|---|---|---|---|
| 5 | 10 | 1:2 | heterogeneous | 0 |
| 5 | 15 | 1:3 | heterogeneous | 1 |
| 5 | 20 | 1:4 | heterogeneous | 7-10 |

Table 2. Injectability of HSA/GA

| HSA% | PVP% | Liquid: Gas | Syringe | Catheter | Time (s) | Foam (mL) | Liquid (mL) |
|---|---|---|---|---|---|---|---|
| 22.5 | 4.5 | 1:3 | 20mL | 5F | 22 | 15 | 1 |

Table 3. Treatment groups and results

| Sheep | BSA(%) | GA(%) | BSA: GA | Sites treated | Size score | Contraction Score | # Sites with hemorrhage/ necrosis |
|---|---|---|---|---|---|---|---|
| 269b | 38 | .25 | 1:152 | 6 | 2.67 | 2.5 | 3 |
| 274 | 34 | .3 | 1:113 | 8 | 2.38 | 2.25 | 2 |
| 266 | 30 | .35 | 1:86 | 8 | 2.13 | 2.38 | 1 |
| 267 | 22.5 | .5 | 1:45 | 8 | 2.38 | 2.13 | 5 |
| 256 | 20 | .75 | 1:27 | 8 | 2.88 | 2.88 | 7 |

Figure 8

Table 4. Treatment results of 25% BSA, 10% PVP and 0.25% GA

| Sheep | Follow-up (days) | Size score | Contraction Score | # Sites with hemorrhage/ necrosis |
|---|---|---|---|---|
| 143 | 6 | 2.75 | 2.63 | 0 |
| 4 | 7 | 1.88 | 2.38 | 0 |
| 253 | 28 | 2.75 | 2.38 | 0 |
| 315 | 57 | 2.38 | 2.25 | 0 |
| 263 | 85 | 2.63 | 2.75 | 0 |

Table 5. Treatment groups

| Sheep | Sites treated | Sides treated | mL liquid | mL oxygen | Follow-up (days) |
|---|---|---|---|---|---|
| 311 | 8 | bilateral | 5 | 15 | 7 |
| 308 | 4 | unilateral | 10 | 20 | 8 |

Table 6. Gross necropsy findings

| Sheep | Size score | Contraction Score | # Sites with hemorrhage/ necrosis |
|---|---|---|---|
| 311 | 2.5 | 2.25 | 0 |
| 308 | 3 | 3 | 1 |

LUNG VOLUME REDUCTION THERAPY USING CROSSLINKED BIOPOLYMERS

RELATED APPLICATIONS

This application claims the benefit of priority to U.S. Provisional Patent Application Ser. No. 60/909,806, filed Apr. 3, 2007.

BACKGROUND

Emphysema is a common form of chronic obstructive pulmonary disease (COPD) that affects between 1.5 and 2 million Americans, and 3 to 4 times that number of patients worldwide. [American Thoracic Society Consensus Committee "Standards for the diagnosis and care of patients with chronic obstructive pulmonary disease," *Am. J. Resp. Crit. Care Med.* 1995, 152, 78-83; and Pauwels, R., et al. "Global strategy for the diagnosis, management, and prevention of chronic obstructive pulmonary disease," *Am. J. Resp. Crit. Care Med.* 2001, 163, 1256-1271.] It is characterized by destruction of the small airways and lung parenchyma due to the release of enzymes from inflammatory cells in response to inhaled toxins. [Stockley, R. "Neutrophils and protease/antiprotease imbalance," *Am. J. Resp. Crit. Care Med.* 1999, 160, S49-S52.] Although this inflammatory process is usually initiated by cigarette smoking, once emphysema reaches an advanced stage, it tends to progress in an unrelenting fashion, even in the absence of continued smoking. [Rutgers, S. R., et al. "Ongoing airway inflammation inpatients with COPD who do not currently smoke," *Thorax* 2000, 55, 12-18.]

The class of enzymes that are responsible for producing tissue damage in emphysema are known as proteases. These enzymes are synthesized by inflammatory cells within the body and when released, they act to degrade the collagen and elastin fibers which provide mechanical integrity and elasticity to the lung. [Jeffery, P. "Structural and inflammatory changes in COPD: a comparison with asthma," *Thorax* 1998, 53, 129-136.] The structural changes that result from the action of these enzymes are irreversible, cumulative, and are associated with loss of lung function that eventually leaves patients with limited respiratory reserve and reduced functional capacity. [Spencer, S. et al. "Health status deterioration inpatients with chronic obstructive pulmonary disease," *Am. J. Resp. Crit. Care Med.* 2001, 163, 122-128; and Moy, M. L., et al. "Health-related quality of life improves following pulmonary rehabilitation and lung volume reduction surgery," *Chest* 1999, 115, 383-389.]

In contrast to other common forms of COPD, such as asthma and chronic bronchitis for which effective medical treatments exist, conventional medical treatment is of limited value in patients with emphysema. Although emphysema, asthma, and chronic bronchitis each cause chronic airflow obstruction, limit exercise capacity, and cause shortness of breath, the site and nature of the abnormalities in asthma and chronic bronchitis are fundamentally different from those of emphysema. In asthma and chronic bronchitis, airflow limitation is caused by airway narrowing due to smooth muscle constriction and mucus hyper-secretion. Pharmacologic agents that relax airway smooth muscle and loosen accumulated secretions are effective at improving breathing function and relieving symptoms. Agents that act in this way include beta-agonist and anti-cholinergic inhalers, oral theophylline preparations, leukotriene antagonists, steroids, and mucolytic drugs.

In contrast, airflow limitation in emphysema is not primarily due to airway narrowing or obstruction, but due to loss of elastic recoil pressure as a consequence of tissue destruction. Loss of recoil pressure compromises the ability to fully exhale, and leads to hyper-inflation and gas trapping. Although bronchodilators, anti-inflammatory agents, and mucolytic agents are frequently prescribed for patients with emphysema, they are generally of limited utility since they are intended primarily for obstruction caused by airway disease; these classes of compounds do nothing to address the loss of elastic recoil that is principally responsible for airflow limitation in emphysema. [Barnes, P. "Chronic Obstructive Pulmonary Disease," *N. Engl. J. Med.* 2000, 343(4), 269-280.]

While pharmacologic treatments for advanced emphysema have been disappointing, a non-medical treatment of emphysema has recently emerged, which has demonstrated clinical efficacy. This treatment is lung volume reduction surgery (LVRS). [Flaherty, K. R. and F J. Martinez "Lung volume reduction surgery for emphysema," *Clin. Chest Med.* 2000, 21(4), 819-48.]

LVRS was originally proposed in the late 1950s by Dr. Otto Brantigan as a surgical remedy for emphysema. The concept arose from clinical observations which suggested that in emphysema the lung was "too large" for the rigid chest cavity, and that resection of lung tissue represented the best method of treatment since it would reduce lung size, allowing it to fit and function better within the chest. Initial experiences with LVRS confirmed that many patients benefited symptomatically and functionally from the procedure. Unfortunately, failure to provide objective outcome measures of improvement, coupled with a 16% operative mortality, led to the initial abandonment of LVRS.

LVRS was accepted for general clinical application in 1994 through the efforts of Dr. Joel Cooper, who applied more stringent pre-operative evaluation criteria and modern post-operative management schemes to emphysema patients. [Cooper, J. D., et al. "Bilateral pneumonectomy for chronic obstructive pulmonary disease," *J. Thorax. Cardiovascular. Surge.* 1995, 109, 106-119.] Cooper reported dramatic improvements in lung function and exercise capacity in a cohort of 20 patients with advanced emphysema who had undergone LVRS. There were no deaths at 90-day follow-up, and physiological and functional improvements were markedly better than had been achieved with medical therapy alone.

While less dramatic benefits have been reported by most other centers, LVRS has nevertheless proven to be effective for improving respiratory function and exercise capacity, relieving disabling symptoms of dispend, and improving quality of life in patients with advanced emphysema. [Gelb, A. F., et al. "Mechanism of short-term improvement in lung function after emphysema resection," *Am. J. Respir. Crit. Care Med.* 1996, 154, 945-51; Gelb, A. F., et al. "Serial lung function and elastic recoil 2 years after lung volume reduction surgery for emphysema," *Chest* 1998, 113(6), 1497-506; Criner, G. and G. E. D'Alonzo, Jr., "Lung volume reduction surgery: finding its role in the treatment of patients with severe COPD," *J. Am. Osteopath. Assoc.* 1998, 98(7), 371; Brenner, M., et al. "Lung volume reduction surgery for emphysema," *Chest* 1996, 110(1), 205-18; and Ingenito, E. P., et al. "Relationship between preoperative inspiratory lung resistance and the outcome of lung-volume-reduction surgery for emphysema," *N. Engl. J. Med.* 1998, 338, 1181-1185.] The benefits of volume reduction have been confirmed in numerous cohort studies, several recently-completed small randomized clinical trials, and the National Emphysema Treatment Trial (NETT). [Goodnight-White, S., et al. "Prospective randomized controlled trial comparing bilateral volume reduction surgery to medical therapy alone inpatients with severe emphysema," Chest 2000, 118(Suppl 4), 1028; Geddes, D., et al. "L-effects of lung volume reduction surgery inpatients with emphysema," N. Eng. J. Med. 2000, 343, 239-245; Pompeo, E., et al. "Reduction pneumoplasty versus respiratory rehabilitation in severe emphysema: a randomized study," Ann. Thorac. Surg. 2000, 2000(70), 948-954; and Fishman, A., et al. "A randomized trial comparing lung-volume-reduction surgery with medical therapy for severe emphysema," N. Eng. J. Med. 2003, 348(21): 2059-73.] On average, 75-80% of patients have experienced a beneficial clinical response to LVRS (generally defined as a 12% or greater improvement in FEV, at 3 month follow-up). The peak responses generally occur at between 3 and 6 months post-operatively, and improvement has lasted several years. [Cooper, J. D. and S. S. Lefrak "Lung-reduction surgery: 5 years on," Lancet 1999, 353(Suppl 1), 26-27; and Gelb, A. F., et al. "Lung function 4 years after lung volume reduction surgery for emphysema," Chest 1999, 116(6), 1608-15.] Results from NETT have further shown that in a subset of patients with emphysema, specifically those with upper lobe disease and reduced exercise capacity, mortality at 29 months is reduced.

Collectively, these data indicate that LVRS improves quality of life and exercise capacity in many patients, and reduces mortality in a smaller fraction of patients, with advanced emphysema. Unfortunately, NETT also demonstrated that the procedure is very expensive when considered in terms of Quality Adjusted Life Year outcomes, and confirmed that LVRS is associated with a 5-6% 90 day mortality. [Chatila, W., S. Furukawa, and G. J. Criner, "Acute respiratory failure after lung volume reduction surgery," Am. J. Respir. Crit. Care Med. 2000, 162, 1292-6; Cordova, F. C. and G. J. Criner, "Surgery for chronic obstructive pulmonary disease: the place for lung volume reduction and transplantation," Curr. Opin. Pulm. Med. 2001, 7(2), 93-104; Swanson, S. J., et al. "No-cut thoracoscopic lung placation: a new technique for lung volume reduction surgery," J. Am. Coll. Surg. 1997, 185(1), 25-32; Sema, D. L., et al. "Survival after unilateral versus bilateral lung volume reduction surgery for emphysema," J. Thorac. Cardiovasc. Surg. 1999, 118(6), 1101-9; and Fishman, A., et al. "A randomized trial comparing lung-volume-reduction surgery with medical therapy for severe emphysema," N. Engl. J. Med. 2003, 348(21), 2059-73.] In addition, morbidity following LVRS is common (40-50%) and includes a high incidence of prolonged post-operative air-leaks, respiratory failure, pneumonia, cardiac arrhythmias, and gastrointestinal complications. Less invasive and less expensive alternatives that could produce the same physiological effect are desirable.

A hydrogel-based system for achieving lung volume reduction has been developed and tested, and its effectiveness confirmed in both healthy sheep, and sheep with experimental emphysema. [Ingenito, E. P., et al. "Bronchoscopic Lung Volume Reduction Using Tissue Engineering Principles," Am. J. Respir. Crit. Care Med. 2003, 167, 771-778.] This system uses a rapidly-polymerizing, fibrin-based hydrogel that can be delivered through a dual lumen catheter into the lung using a bronchoscope. The fibrin-based system effectively blocks collateral ventilation, inhibits surfactant function to promote collapse, and initiates a remodeling process that proceeds over a 4-6 week period. Treatment results in consistent, effective lung volume reduction. These studies have confirmed the safety and effectiveness of using fibrin-based hydrogels in the lung to achieve volume reduction therapy.

SUMMARY

One aspect of the invention relates to bronchoscopic lung volume reduction using a composition comprising a crosslinker, a biopolymer that can be polymerized in situ with the crosslinker, and a polymeric additive, which accelerates the cross-linking reaction. In certain embodiments, the composition comprising a crosslinker, polymeric additive, and biopolymer is in the form of a gel or foam. In certain embodiments, the biopolymer contains a plurality of free amino groups. In certain embodiments, the biopolymer is a protein, polysaccharide or polynucleotide. In certain embodiments, the biopolymer is a protein. In certain embodiments, the biopolymer is a protein selected from the group consisting of actin, albumin, alpha-globulin, beta-globulin, gamma-globulin, cadherin, calmodulin, calbindin, casein, catenin, collagens, C-reactive protein, cholesterylester transfer protein, cytokines, DNA binding proteins, dystrophin, elastin, ferritin, fetuin, fibrinogen, fibrin, fibroin, fibronectin, gelatin, hemoglobin, histones, insulin, epidermal growth factor, heparin, interleukins, insulin-like growth factor, integrin, keratin, kinases, laminin, lysozyme, myoglobin, myosin, reelin, rhodopsin, selectin, transthyretin, thrombin, tubulin, trypsin, utrophin, and vinculin. In certain embodiments, the biopolymer is albumin. Another aspect of the invention relates to bronchoscopic lung volume reduction using gels or foams generated from solutions of biopolymers which contain free amine groups that can be polymerized in situ with di-, tri, or poly-aldehydes. Yet another aspect of the invention relates to a method of bronchoscopic lung volume reduction using a cross-linked gel or foam generated from a solution of an albumin protein, which contains free amine groups, that can be polymerized in situ via an aldehyde-containing cross-linker; and a polymeric additive which accelerates the cross-linking reaction. In certain embodiments, the albumin protein is a mammalian serum albumin. In certain embodiments, the albumin protein is bovine serum albumin or human serum albumin. In certain embodiments, the aldehyde-containing cross-linker is a dialdehyde. In certain embodiments, the aldehyde-containing cross-linker is glutaraldehyde. In certain embodiments, the compositions and methods cause minimal toxicity, are injectable through a catheter, and polymerize rapidly enough to prevent solution from spilling back into the airways following injection.

In certain embodiments, the above-mentioned method for reducing lung volume in a patient comprises the steps of administering to a region of the lungs of a patient a composition comprising a biopolymer, a cross-linker, and a polymeric additive; wherein said polymeric additive accelerates a cross-linking reaction between the biopolymer and the cross-linker. In certain embodiments, the composition is administered using a bronchoscope or catheter. In certain embodiments, the above-mentioned method for reducing lung volume in a patient further comprises the step of advancing into a region of a patient's lung via said patient's trachea a catheter lumen through a bronchoscope. In certain embodiments, the composition is a foam or gel. In certain embodiments, the composition is a foam. In certain embodiments, the composition is a gel. In certain embodiments, the composition further comprises a gas. In certain embodiments, the above-mentioned method for reducing lung volume in a patient comprises the steps of advancing into a region of a patient's lung via said patient's trachea a catheter lumen through a bronchoscope; and administering, through the catheter, a gel or foam composition comprising an albumin protein, a cross-linker, and a polymeric additive; wherein said polymeric additive accelerates a cross-linking reaction between the albumin protein and the cross-linker. In certain embodiments the gel or foam composition is formed by combining the albumin protein, the cross-linker, and the polymeric additive and then foaming the mixture with a gas.

Because of the relatively slow polymerization in some embodiments, there is time to foam the solution prior to administration to the patient. Alternatively, the gel or foam composition is formed by combining the albumin protein and the polymeric additive and then foaming the mixture; to this mixture is added the cross-linker. In both cases, a foam composition is administered to the patient (e.g., via a single lumen catheter), and results in a cross-linked foam in the patient's lung. In certain embodiments, the compositions and methods described herein are intended for use in the treatment of patients with emphysema.

It should be appreciated that compositions of the invention also may include one or more additional compounds (e.g., therapeutic compound(s), stabilizing compound(s), antibiotic(s), growth factor(s), etc.), buffers, salts, surfactants, anti-surfactants, lipids, excipients, and/or other suitable compounds. In certain embodiments, compositions of the invention may be sterilized.

In certain embodiments, compositions of the invention may be used to promote one or more of the following responses when contacted to a tissue in a body: sclerosis (hardening of tissue), fibrosis (excess fibrous connective tissue), wound healing, tissue sealing, local microvascular thrombosis (blood clot), cellular necrosis or apoptosis (cell death), tumor regression, cell lysis, or any combination thereof.

Additional advantages and novel features of the present invention will become apparent from the following detailed description of various non-limiting embodiments of the invention.

BRIEF DESCRIPTION OF THE FIGURES

FIG. 3 depicts two graphs showing the effects of adding 5, 10 or 15% [A] polyvinylpyrrolidone (PVP) or [B] dextran to a mixture of 25% albumin and 0.25% glutaraldehyde (GA) at room temperature.

FIG. 7 depicts Table 1, showing the foamability of a mixture of 22.5% human serum albumin with 4.5% polyvinylpyrrolidine; Table 2, showing the injectability of a the same human serum albumin and glutaraldehyde mixture; and Table 3, showing treatment groups and results for various bovine serum albumin and glutaraldehyde mixtures.

FIG. 8 depicts Table 4, showing treatment results obtained with a mixture of 25% BSA, 10% PVP and 0.25% GA; Table 5, showing treatment groups corresponding to administration of the same mixture; and Table 6, showing gross necropsy findings corresponding to administration of the same mixture.

DETAILED DESCRIPTION

Figure 1:
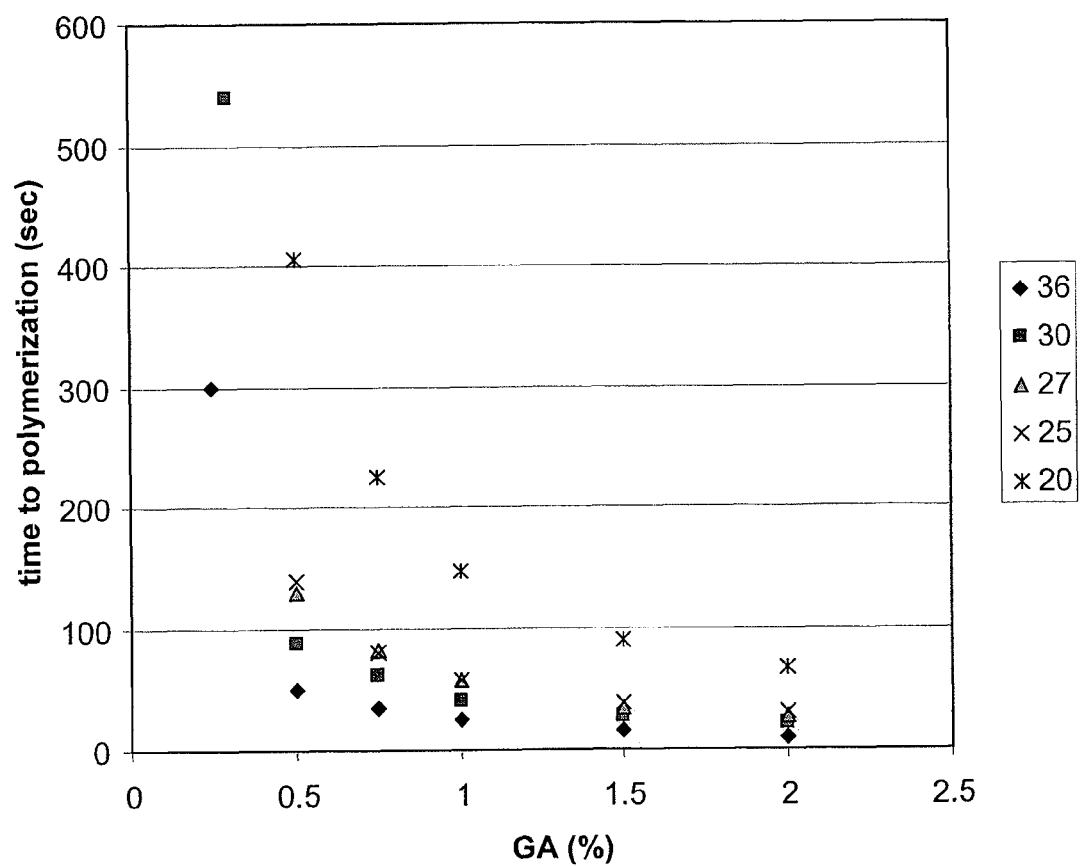
FIG. 1 depicts a graph showing the effects of albumin and glutaraldehyde (GA) concentration on polymerization time at room temperature. Each data set corresponds to a different albumin concentration from 20 to 36%.

One aspect of the invention relates to compositions and methods for treatment of patients with advanced emphysema. In certain embodiments, the invention relates to a system for achieving lung volume reduction therapy, wherein a composition is injected into the lung. In certain embodiments, the composition is a foam or gel. In certain embodiments, the composition is a foam. In certain embodiments, the composition is a gel. In certain embodiments, the invention relates to a system for achieving lung volume reduction therapy, wherein a composition is injected into the lung as a gas-containing foam. Delivery of the inventive compositions may follow an initial pretreatment designed to prime the treatment area by causing collapse and/or by removing the surface lining cells of the treatment area. However, certain inventive compositions can, by themselves, provide this function and do not require pretreatment.

The compositions in various forms (e.g., foam or gel) serve several key functions that are beneficial for promoting lung volume reduction: blocking collateral ventilation by coating the interstices of the lung surface, a step that prevents rapid re-inflation of the treatment area; ensuring that reagents remain localized to the treatment area, since upon polymerization, the foam or gel becomes trapped in the small airways and alveoli of the lung, preventing flow beyond the intended treatment site; and filling the treatment area, displacing air and forming a bridge between adjacent regions of lung tissue.

In certain embodiments, to be effective as a volume reducing agent in the lung, the precursors of the cross-linked foam or gel composition must have sufficiently fast polymerization kinetics and physical properties to allow for endoscopic delivery. The compositions must have favorable biocompatibility profiles, show rapid polymerization, and have mechanical properties such that following polymerization the firmness of the foam or gel composition does not mechanically injure adjacent soft lung tissues. Further, the compositions must have initial viscosities that will allow them to be injected through a small-bore catheter. In addition, the foam or gel composition must have acceptable pharmacokinetic degradation profiles in vivo. The inventive compositions described herein which posses some or all of these features should be satisfactory for achieving bronchoscopic lung volume reduction therapy.

Herein are described cross-linked biopolymer (e.g., albumin) albumin foams or gels that possess some or all of these properties. In addition, in certain embodiments, the cross-linked albumin foams or gels of the invention may show superior properties to some known LVRT compositions because of improved tissue adhesion; the foams or gels of the invention may have minimal seepage and may be self-healing (i.e., substantially less cracks or breaks might be formed in the solidified mass).

It is known that albumin proteins and glutaraldehyde can be combined to form a rapidly polymerizing, biocompatible tissue glue: Bioglue® is a commercially available albumin/glutaraldehyde tissue glue which contains 36 w % bovine serum albumin and 2 w % GA (final concentrations after mixing). However, in order for such a glue to be efficacious for bronchoscopic lung volume reduction (BLVR), it must have specific properties, including: a polymerization time long enough to allow delivery to the lung via a bronchoscopically placed catheter (greater than about 1 min); fluid mechanical properties that allow injection through a bronchoscopically-guided small bore catheter; and polymerization time short enough to allow practical procedure length without spillage from the treatment site (less than about 5 minutes). Because of the rapid rate of polymerization of Bioglue® (less than thirty seconds; data not shown), the Bioglue® composition is not well suited for LVRT. Moreover, decreasing the ratio of bovine serum albumin to glutaraldehyde in order to achieve the desired polymerization kinetics results in a glutaraldehyde concentration which is highly toxic. Glutaraldehyde toxicity is well known. See, for example, Speer, D. P. et al. *J. Biomedical Mat. Res.* 1980, 14, 753-764; Huang-Lee, L. L. H. et al. *J. Biomedical Mat. Res.* 1990, 24, 1185-1201; Fürst, W. et al. *Ann. Thorac. Surg.* 2005, 79, 1522-1529; and Zeiger, E. et al. *Mutation Res.* 2005, 589, 136-151.

Remarkably, as disclosed herein, the use of a polymeric additive enables compositions that foam or gel with the desired characteristics. There are many advantages to the compositions and methods described herein. In some respects, the compositions described herein are chemically simpler that current LVRT compositions. In certain embodiments, the chemicals are less expensive. In certain embodiments, the foams and gels of the invention have better space filling characteristics than fibrin-based hydrogel systems, meaning that smaller amounts of material can be used to collapse larger lung volumes. In addition, in certain embodiments, there appears to be less potential for systemic toxicity than with some other LVRT approaches.

Definitions

For convenience, certain terms employed in the specification and appended claims are collected here. These definitions should be read in light of the entire disclosure and understood as by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "biodegradable" is intended to mean any component capable of disappearing by progressive degradation (metabolism).

The term "contrast-enhancing" refers to materials capable of being monitored during injection into a mammalian subject by methods for monitoring and detecting such materials, for example by radiography or fluoroscopy. An example of a contrast-enhancing agent is a radiopaque material. Contrast-enhancing agents including radiopaque materials may be either water soluble or water insoluble. Examples of water soluble radiopaque materials include metrizamide, iopamidol, iothalamate sodium, iodomide sodium, and meglumine. Examples of water insoluble radiopaque materials include metals and metal oxides such as gold, titanium, silver, stainless steel, oxides thereof, aluminum oxide, zirconium oxide, etc.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_1$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl, cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocycles.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidone, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, fluoroalkyl, cyano, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, fluoroalkyl, cyano, or the like.

The term "carbocyclyl" or "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to SH; the term "hydroxyl" means —OH; and the term "sulfonyl" is art-recognized and refers to —$SO_2$—. "Halide" designates the corresponding anion of the halogens, and "pseudohalide" has the definition set forth in "Advanced Inorganic Chemistry" by Cotton and Wilkinson.

The terms "amine" and "amino" are art-recognized and refer to both unsubstituted and substituted amines.

The term "amido" is art recognized as an amino-substituted carbonyl.

The term "alkylthio" refers to an alkyl group, as defined above, having a sulfur radical attached thereto.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

Aliphatic is a $C_1$-$C_{12}$ chain, wherein one or more carbon atoms is optionally substituted with a heteroatom selected from the group consisting of oxygen, nitrogen or sulfur. Each carbon is optionally substituted with a functional group selected from the group consisting of hydroxyl, thiol, amino, alkyl, alkoxy, thioalkyl, amionalkyl, aryl, aryloxy, thioaryl, arylamino, heteroaryl and cycloalkyl. Aliphatic also includes optionally substituted $C_1$-$C_{12}$ alkenyl and alkynyl groups. Straight-chain or branched $C_1$-$C_{12}$-alkyl group is selected from the group consisting of methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl and decyl.

Cycloaliphatic is a $C_3$-$C_7$ cycloalkyl selected from the group consisting of cyclopropyl, cyclobutyl, cyclopentyl, cyclohexyl and cycloheptyl. The $C_3$-$C_7$ cycloalkyl is optionally substituted with 1, 2, 3, 4 or 5 substituents selected from the group consisting of hydroxyl, thiol, amino, alkyl, alkoxy, thioalkyl, amionalkyl, aryl, aryloxy, thioaryl, arylamino, heteroaryl and cycloalkyl.

Aromatic is an aryl group selected from the group consisting of phenyl, tolyl, xylyl, mesityl, naphthyl, fluorenyl, anthracenyl, phenanthrenyl, pyridyl, and naphthacenyl, wherein the aryl group is optionally substituted with 1, 2, 3, 4 or 5 substituents selected from the group consisting of alkyl, alkoxy, thioalkyl, amino, nitro, trifluoromethyl, aryl, halo and cyano. Aromatic dialdehydes include isophthalaldehyde, phthalaldehyde and terephthalaldehyde.

Heterocycloaliphatic is a $C_4$-$C_7$ ring optionally substituted with 1, 2 or 3 heteroatoms selected from the group consisting of oxygen, nitrogen and sulfur. Each carbon is optionally substituted with a functional group selected from the group consisting of hydroxyl, thiol, amino, alkyl, alkoxy, thioalkyl, amionalkyl, aryl, aryloxy, thioaryl, arylamino, heteroaryl and cycloalkyl. Heterocycloaliphatic group includes pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl and dioxanyl.

Heterocyclic is a heterocycloaromatic selected from the group consisting of pyridyl, quinolinyl, acridinyl, pyridazinyl, pyrimidinyl and pyrazinyl, wherein the heterocycloaromatic is optionally substituted with 1, 2 or 3 substituents selected from the group consisting of alkyl, alkoxy, thioalkyl, amino, nitro, trifluoromethyl, aryl, halo and cyano.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

Certain compounds contained in compositions of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

Biopolymers

The biopolymers for use in the present invention can be proteins, polysaccharides or polynucleotides, wherein the monomer units are amino acids, saccharides or nucleic acids, respectively. Examples of biopolymers include, but are not limited to actin, albumin, alpha-globulin, beta-globulin, gamma-globulin, cadherin, calmodulin, calbindin, casein, catenin, celluloses, chitin, collagens, C-reactive protein, cholesterylester transfer protein, chondroitin sulfate, cytokines, DNA, DNA binding proteins, dystrophin, elastin, ferritin, fetuin, fibrinogen, fibrin, fibroin, fibronectin, gelatin, hemoglobin, histones, insulin, epidermal growth factor, heparin, interleukins, insulin-like growth factor, integrin, keratan sulfate, keratin, kinases, laminin, lysozyme, myoglobin, myosin, reelin, rhodopsin, RNA, selectin, transthyretin, thrombin, tubulin, trypsin, utrophin and vinculin.

In certain embodiments, the biopolymer of the present invention is a poly(amino acid), comprising at least 90% of amino acids selected from the group consisting of alanine, arginine, asparagine, aspartic acid, cysteine, glutamic acid, glutamine, glycine, histidine, isoleucine, leucine, methionine, phenylalanine, serine, threonine, tyrosine and valine; and no more than 10% of amino acids selected from the group consisting of lysine and tryptophan.

In certain embodiments, the biopolymer of the present invention is a poly(aminosaccharide) of formula I or II:

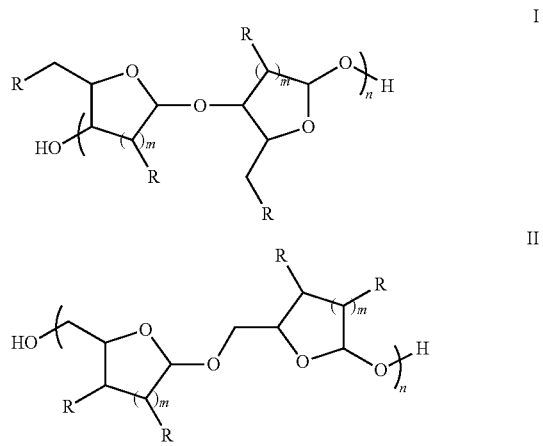

wherein independently for each occurrence:
m is 1 or 2;
R is OH or NH$_2$; and
the stereochemical configuration at a stereocenter is R or S.

Albumins

Albumin refers generally to any protein with water solubility, which is moderately soluble in concentrated salt solutions, and which experiences heat coagulation (protein denaturation). Substances containing albumin, such as egg white, are called albuminoids. The most well-known type of albumin is serum albumin in the blood, but there is also the storage protein ovalbumin in egg white, and other storage albumins in the seeds of some plants.

Serum albumin is the most abundant blood plasma protein and is produced in the liver and forms a large proportion of all plasma protein. Human serum albumin, a water-soluble protein of 585 amino acids with a molecular weight of 66 kD, is the most abundant protein in plasma (3.5-5.0 g/100 mL in blood plasma), but also exists in lower concentrations in extra vascular fluids. It has a large number of charged amino acids (about 100 negative charges and 100 positive charges) with an isoelectric point of 5.0 and a net negative charge of −15 at a plasma pH of 7.4, and attracts both anions and cations. In certain embodiments, the albumin protein of the invention is a mammalian serum albumin, human serum albumin, porcine serum albumin and/or bovine serum albumin. In certain embodiments, the albumin protein of the invention is a human serum albumin and/or bovine serum albumin. In certain embodiments, the albumin protein of the invention is a human serum albumin. In certain embodiments, the albumin is a recombinant protein.

Cross-Linkers

One embodiment of the present invention relates to the cross-linking of biopolymers (e.g., albumin proteins). It is well known in the art that bifunctional "cross-linking" reagents contain two reactive groups, thus providing a means of covalently linking two target groups. When the biopolymer to be cross-linked comprises nucleophilic moieties, the reactive groups in a chemical cross-linking reagent typically belong to the classes of electrophilic functional groups, e.g., succinimidyl esters, maleimides, idoacetamides, and aldehydes. However, when the biopolymer to be cross-linked comprises electrophilic moieties, the reactive groups in a chemical cross-linker may be nucleophilic functional groups, e.g., alcohols, thiols and amines. Bifunctional cross-linking reagents can be divided in homobifunctional, heterobifunctional and zero-length bifunctional cross-linking reagents. In homobifunctional cross-linking reagents, the reactive groups are identical. In heterobifunctional cross-linking reagents, the reactive groups are not identical. The "zero-length" cross-linking reagent forms a chemical bond between two groups utilizing a single functional group (e.g., a carbonyl moiety derived from carbonyl diimidazole) or without itself being incorporated into the product. For example, a water-soluble carbodiimide (EDAC) may be used to couple carboxylic acids to amines. In addition to the traditional bifunctional cross-linking reagents, a noncovalent interaction between two molecules that has very slow dissociation kinetics can also function as a crosslink. For example, reactive derivatives of phospholipids can be used to link the liposomes or cell membranes to antibodies or enzymes. Biotinylation and haptenylation reagents can also be thought of as heterobifunctional cross-linking reagents because they comprise a chemically reactive group as well as a biotin or hapten moiety that binds with high affinity to avidin or an anti-hapten antibody, respectively.

In certain embodiments, the cross-linkers of the present invention are homobifunctional cross-linkers (e.g., dialdehydes). In other embodiments, the cross-linkers of the present invention are homopolyfunctional cross-linking reagents.

In certain embodiments, the cross-linkers of the present invention are di- or polyaldehydes. As will be appreciated by one skilled in the art, aldehydes described herein can exist as hydrates in aqueous solution, e.g., existing as hemi-acetals in aqueous solution. In certain embodiments, such hydrates can revert back to the corresponding aldehyde and/or ketone for cross-linking. In some embodiments, hydrates of aldehydes and/or hydrates of other cross-linking activating moieties are themselves capable of bringing about cross-linking.

In certain embodiments, the cross-linker of the invention is W—X$_n$—W, wherein independently for each occurrence,
W is

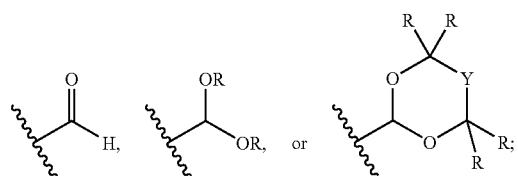

X is —C(R)$_2$—; or, for at most two, three, four, five, six, seven or eight occurrences, X is —C(=O)—, —O—, —S—, —N(R)—, —N(C(O)R)—, —C(R)=C(R)—, —C≡C—, —C≡N—, —C(R)=N—, a cycloalkyl diradical, a heterocycloalkyl diradical, an aryl diradical, or a heteroaryl diradical;

Y is a bond, —C(R)$_2$—, —C(=O)—, —O—, —S—, —N(R)—, or —N(C(O)R)—;

R is hydrogen, alkyl, lower alkyl, carbocyclyl, alkenyl, lower alkenyl, alkynyl, lower alkynyl, aryl, heteroaryl, aralkyl, or heteroaralkyl; and n is 1-20 inclusive.

In certain embodiments, the present invention relates to the aforementioned cross-linker, wherein W is

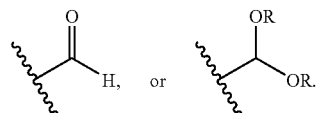

In certain embodiments, the present invention relates to the aforementioned cross-linker, wherein W is

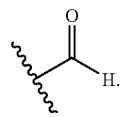

In certain embodiments, the present invention relates to the aforementioned cross-linker, wherein W is

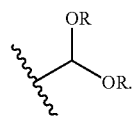

In certain embodiments, the present invention relates to the aforementioned cross-linker, wherein X is —CR$_2$—. In certain embodiments, the present invention relates to the aforementioned cross-linker, wherein X is —CH$_2$—.

In certain embodiments, the present invention relates to the aforementioned cross-linker, wherein Y is a bond, —CR$_2$—, or —O—. In certain embodiments, the present invention relates to the aforementioned cross-linker, wherein Y is a bond, or —CH$_2$—.

In certain embodiments, the present invention relates to the aforementioned cross-linker, wherein R is hydrogen or lower alkyl. In certain embodiments, the present invention relates to the aforementioned cross-linker, wherein R is hydrogen.

In certain embodiments, the present invention relates to the aforementioned cross-linker, wherein n is 1-10 inclusive. In certain embodiments, the present invention relates to the aforementioned cross-linker, wherein n is 2. In certain embodiments, the present invention relates to the aforementioned cross-linker, wherein n is 3. In certain embodiments, the present invention relates to the aforementioned cross-linker, wherein n is 4. In certain embodiments, the present invention relates to the aforementioned cross-linker, wherein n is 5. In certain embodiments, the present invention relates to the aforementioned cross-linker, wherein n is 6.

In certain embodiments, the cross-linker is glutaraldehyde. As mentioned above, it has been found that the absolute local concentration of glutaraldehyde must be maintained at or below a level that does not produce undesired excessive local toxicity. At concentrations of 0.75% or greater, glutaraldehyde produces significant tissue necrosis. Concentrations below this level produce limited local toxicity associated with clinically acceptable side effects. In other embodiments, other di- and polyaldehydes, such as glyoxal may be used.

In certain embodiments, the crosslinker of the present invention is represented by the following formula:

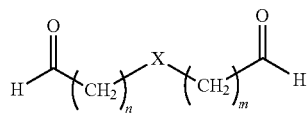

wherein independently for each occurrence
n is 0-12;
m is 0-12; and
X is a di-radical of an aliphatic, cycloaliphatic, aromatic, heterocycloaliphatic or heterocyclic moiety.

In certain embodiments, the crosslinker of the invention is represented by the following formula:

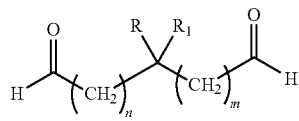

wherein independently for each occurrence
n is 0-12;
m is 0-12; and
R and $R_1$ are each independently hydrogen, aliphatic, cycloaliphatic, aromatic, heterocycloaliphatic or heterocyclic moiety.

In certain embodiments, the cross-linker is of biological origin. In certain embodiments, the cross-linker is an aldehyde. In certain embodiments, said aldehyde is an oxidized polysaccharide. In certain embodiments, the aldehyde is an oxidized polysaccharide, the polysaccharide being at least one from the group of dextran, chitin, starch, agar, cellulose, alginic acid, glycosaminoglycans, hyaluronic acid, chondroitin sulfate and derivatives thereof. In certain embodiments, the aldehyde is dextranaldehyde. The aldehyde, especially the dextranaldehyde, preferably has a molecular weight of about 60,000 to 600,000, in particular about 200,000. Higher molecular weights, in particular of at least 200,000, may result in high degrees of crosslinking.

In certain embodiments, the aldehyde cross-linker is advantageously partially or completely masked. The purpose of the masking, especially of oxidized polyaldehydes, is to prevent the formation of intermolecular acetals and thus ensure the stability of the solutions.

In certain embodiments, a method of the invention results in overall lung volume reduction of about 0.5% to about 40%. In certain embodiments, a method of the invention results in overall lung volume reduction of about 0.5% to about 30%. In certain embodiments, a method of the invention results in overall lung volume reduction of about 0.5% to about 20%. In certain embodiments, a method of the invention results in overall lung volume reduction of about 0.5% to about 10%. Such reduction may be achieved upon a single or multiple administrations of compositions of the present invention.

Ratio of Biopolymer to Cross-Linker

As mentioned above, one of the drawbacks to some known cross-linked albumin compositions is that the high concentration of cross-linker needed to achieve workable polymerization kinetics leads to toxicity. One aspect of the present invention relates to compositions wherein the ratio of the biopolymer to the cross-linker is greater than about 20:1. In certain embodiments, the ratio of the biopolymer to the cross-linker is greater than about 30:1; about 40:1; about 50:1; about 60:1; about 70:1; about 80:1; about 90:1; about 100:1; about 110:1; about 120:1; about 130:1; about 140:1; about 150:1; about 160:1; about 170:1; about 180:1; about 190:1; or about 200:1. All ratios are weight ratios; in other words, a ratio of about 20:1 means the weight of the biopolymer is about twenty times the weight of the cross-linker.

Cross-Linking Rate Modifiers

In certain embodiments, a polymeric additive may be used as a rate modifier to modify the rate of the cross-linking reaction. In certain embodiments, the polymeric additives may accelerate the formation of a Schiff base between amines in the biopolymers and aldehydes in the cross-linker. While not intending to be bound by any mechanistic theory, the effect of the polymeric additives may be to sequester water and thus increase the effective concentration of cross-linker. Alternatively, or in addition, the polymeric additives may catalytically, perhaps through hydrogen bonding, accelerate the cross-linking reaction.

In certain embodiments, the polymeric additive is based on polymers of vinylpyrrolidone.

The structure of vinylpyrrolidone is

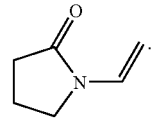

In certain embodiments, the polymeric additive is poly(vinylpyrrolidone). In other embodiments, the polymer of the invention is a copolymer of vinyl pyrrolidone. For example, polymeric additives of the invention include vinylpyrrolidone/dimethylaminoethyl methacrylate copolymer, vinylpyrrolidone/styrene copolymer, and vinylpyrrolidone/vinyl acetate copolymer. In certain copolymers there is about 25 mol % vinylpyrrolidone; about 40 mol % vinylpyrrolidone; about 50 mol % vinylpyrrolidone; about 60 mol % vinylpyrrolidone; about 75 mol % vinylpyrrolidone; about 85 mol % vinylpyrrolidone; or about 95 mol % vinylpyrrolidone.

In certain embodiments, the polymeric additive is based on dextran. Dextran is a complex, branched polysaccharide made of many glucose molecules joined into chains of varying lengths. The straight chain consists of α1→6 glycosidic linkages between glucose molecules, while branches begin from α1→3 linkages (and in some cases, α1→2 and α1→4 linkages as well). Dextran is synthesized from sucrose by *Leuconostoc mesenteroides streptococcus* and *Streptococcus mutans* and is also produced by bacteria and yeast.

In certain embodiments, the polymeric additive is based on ethylene glycol polymers. Polyethylene glycol (PEG) and polyethylene oxide (PEO) are polymers composed of repeating subunits of identical structure, called monomers, and are the most commercially important polyethers. Poly (ethylene glycol) or poly (ethylene oxide) refers to an oligomer or polymer of ethylene oxide. The two names are chemically synonymous, but historically PEG has tended to refer to shorter polymers, PEO to longer. As used herein, polyethylene glycol refers to both PEG and PEO. PEG and PEO are liquids or low-melting solids, depending on their molecular weights. Both are prepared by polymerization of ethylene oxide. While PEG and PEO with different molecular weights find use in different applications and have different physical properties (e.g., viscosity) due to chain length effects, their chemical properties are nearly identical. Derivatives of PEG and PEO are in common use, the most common derivative being the methyl ether (methoxypoly (ethylene glycol)), abbreviated mPEG. Their melting points vary depending on the formula weight of the polymer. PEG or PEO has the following structure: $HO(CH_2CH_2O)_rH$. The numbers that are often included in the names of PEGs and PEOs indicate their average molecular weights, e.g., a PEG with r equal to about 80 would have an average molecular weight of approximately 3500 Daltons and would be labeled PEG 3500.

In certain embodiments the polymeric additive is based on acrylic acid polymers. Carbomer is a non-proprietary name for these materials. They are high molecular weight polymers prepared by cross-linking acrylic acids with the likes of allyl ether pentaerythritol, allyl ether of sucrose, or allyl ether of propylene. Such polymers also go by the names Acritamer® or Carbopol®. The chemical name and CAS registry number for the class is carboxypolymethylene [54182-57-9]. Exemplary carbomers are carbomer 910 [91315-32-1], carbomer 934 [9007-16-3], carbomer 934P [9003-01-4] and carbomer 940 [76050-42-5]. These polymers contain between 56-68% of carboxylic acid groups, calculated on a dry basis. A blend of two or more carbomers of differing molecular weight may be used to modify and manipulate the polymerization rate.

Many of the polymers above are produced as mixtures of molecules with a distribution of molecular weights, i.e., they are polydisperse. The size distribution can be characterized statistically by its weight average molecular weight ($M_w$) and its number average molecular weight ($M_n$), the ratio of which is called the polydispersity index ($M_w/M_n$). $M_w$ and $M_n$ can be measured by mass spectroscopy.

In certain embodiments, the cross-linking reaction substantially occurs in less than or equal to about 1 minute, less than or equal to about 90 seconds, less than or equal to about 2 minutes, less than or equal to about 150 seconds, less than or equal to about 3 minutes, less than or equal to about 4 minutes, less than or equal to about 5 minutes, less than or equal to about 6 minutes, less than or equal to about 10 minutes.

Compositions

In certain embodiments, the present invention relates to compositions wherein the biopolymer is about 10-40% by weight of said composition. In certain embodiments, the biopolymer is about 15-35% by weight of said compositions. In certain embodiments, the biopolymer is about 20-30% by weight of said composition. In certain embodiments, the biopolymer is about 25% by weight of said composition. In certain embodiments, the biopolymer is about 22.5% by weight of said composition.

In certain embodiments, the present invention relates to compositions wherein the crosslinker is about 0.1-2% by weight of said composition. In certain embodiments, the crosslinker is about 0.1-1% by weight of said composition. In certain embodiments, the crosslinker is about 0.1-0.5% by weight of said composition. In certain embodiments, the crosslinker is about 0.3% by weight of said composition. In certain embodiments, the crosslinker is about 0.25% by weight of said composition.

In certain embodiments, the present invention relates to compositions wherein the polymeric additive is about 0-15% by weight of said composition. In certain embodiments, the polymeric additive is about 2-12% by weight of said composition. In certain embodiments, the polymeric additive is about 10% by weight of said composition. In certain embodiments, the polymeric additive is about 4.5% by weight of the composition.

In certain embodiments, the present invention relates to compositions wherein the biopolymer is about 10-40% by weight of said composition; the crosslinker is about 0.1-2% by weight of said composition; and the polymeric additive is about 0-15% by weight of said composition. In certain embodiments, the biopolymer is about 25% by weight of said composition; the crosslinker is about 0.25% by weight of said composition; and the polymeric additive is about 10% by weight of said composition. In certain embodiments, the biopolymer is about 22.5% by weight of said composition, the crosslinker is about 0.3% by weight of said composition; and the polymeric additive is about 4.5% by weight of the composition.

In certain embodiments, the present invention relates to compositions, wherein bovine serum albumin is about 25% by weight of said composition, GA is about 0.25% by weight of the composition; and PVP is about 10% by weight of said compositions. In certain embodiments, human serum albumin is about 22.5% by weight of said composition, GA is about 0.3% by weight of said composition; and PVP is about 4.5% by weight of said composition.

Foaming Modifiers

In certain embodiments, a foaming modifier facilitates the generation of a stable foam. In other words, in certain embodiments a foaming modifier may be introduced into an inventive composition to facilitate the formation of a foamed composition. Examples of such a foaming modifier include tissue compatible surfactants, tyloxapol, poloxamers, poloxamines, phospholipids, and glycerol. Illustrative of these foaming modifiers are non-toxic surfactants including, but are not limited to, fats or proteins in edible foams. However, the surfactant may be an ionic or non-ionic surfactant depending on the intended application. The ionic surfactants including, for example, anionic surfactants, such as sodium stearate, sodium dodecyl sulfate, α-olefinsulfonate and sulfoalkylamides and cationic surfactants, such as alkyldimethylbenzylammonium salts, alkyltrimethylammonium salts and alkylpyridinium salts; and amphoteric surfactants such as imidazoline surfactants. The non-ionic surfactants include, for example, polyethylene oxide alkyl ethers, polyethylene oxide alkylphenyl ethers, glycerol fatty acid esters, sorbitan fatty acid esters, sucrose fatty acid esters, and the like.

Additional surfactants which may be used include surfactants such as Triton x-100, beractant, colfosceril, and/or palmitate; anionic surfactants such as sodium tetradecyl sulfate; cationic surfactants such as tetrabutylammonium bromide and/or butyrylcholine chloride; nonionic surfactants such as polysorbate 20 (e.g., Tween 20), polysorbate 80 (e.g., Tween 80), and/or poloxamers; amphoteric and/or zwitterionic surfactants such as dodecyldimethyl(3-sulfopropyl)ammonium hydroxide, inner salt; amines, imines and/or amides, such as arginine, imidazole, povidine, tryptamine, and/or urea; alcohols such as ascorbic acid, ethylene glycol, methyl gallate, tannins and/or tannic acid; phosphines, phosphites and phosphonium salts, such as triphenylphosphine and/or triethyl phosphite; inorganic bases and/or salts, such as calcium sulfate, magnesium hydroxide, sodium silicate, and/or sodium bisulfite; sulfur compounds such as polysulfides and/or thiourea; polymeric cyclic ethers such as calixarenes, crown ethers, monensin, nonactin, and/or polymeric epoxides; cyclic and acyclic carbonates; organometallics (e.g., naphthenate and manganese acetylacetonate); phase transfer catalysts (e.g., Aliquat 336); and radical initiators and radicals (e.g., di-t-butyl peroxide and/or azobisisobutyronitrile).

Therapeutic Agents

Any of a vast number of therapeutic agents may be incorporated in the foams or gels used in the methods of the present invention. In general, therapeutic agents which may be incorporated include, without limitation: antiinfectives such as antibiotics and antiviral agents (as mentioned above); analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins. Suitable pharmaceuticals for parenteral administration are well known as is exemplified by the Handbook on Injectable Drugs, 6$^{th}$ Edition, by Lawrence A. Trissel, American Society of Hospital Pharmacists, Bethesda, Md., 1990 (hereby incorporated by reference).

The pharmaceutically active compound may be any substance having biological activity, including proteins, polypeptides, polynucleotides, nucleoproteins, polysaccharides, glycoproteins, lipoproteins, and synthetic and biologically engineered analogs thereof. The term "protein" is art-recognized and for purposes of this invention also encompasses peptides. The proteins or peptides may be any biologically active protein or peptide, naturally occurring or synthetic.

Examples of proteins include antibodies, enzymes, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the numerous analogues and congeners of the foregoing molecules. The pharmaceutical agents may be selected from insulin, antigens selected from the group consisting of MMR (mumps, measles and rubella) vaccine, typhoid vaccine, hepatitis A vaccine, hepatitis B vaccine, herpes simplex virus, bacterial toxoids, cholera toxin B-subunit, influenza vaccine virus, bordetela pertussis virus, vaccinia virus, adenovirus, canary pox, polio vaccine virus, *plasmodium falciparum, bacillus* calmette geurin (BCG), *klebsiella pneumoniae*, HIV envelop glycoproteins and cytokins and other agents selected from the group consisting of bovine somatropine (sometimes referred to as BST), estrogens, androgens, insulin growth factors (sometimes referred to as IGF), interleukin I, interleukin II and cytokines. Three such cytokines are interferon-β, interferon-γ and tuftsin.

Examples of bacterial toxoids that may be incorporated in the foams or gels used in the methods of the invention are tetanus, diphtheria, pseudomonas A, mycobaeterium tuberculosis. Examples of that may be incorporated in the compositions used in the occlusion methods of the invention are HIV envelope glycoproteins, e.g., gp 120 or gp 160, for AIDS vaccines. Examples of anti-ulcer H2 receptor antagonists that may be included are ranitidine, cimetidine and famotidine, and other anti-ulcer drugs are omparazide, cesupride and misoprostol. An example of a hypoglycaemic agent is glizipide.

Classes of pharmaceutically active compounds which can be loaded into that may be incorporated in the foams or gels used in the methods of the invention include, but are not limited to, anti-AIDS substances, anti-cancer substances, antibiotics, immunosuppressants (e.g., cyclosporine) anti-viral substances, enzyme inhibitors, neurotoxins, opioids, hypnotics, antihistamines, lubricants tranquilizers, anti-convulsants, muscle relaxants and anti-Parkinson substances, antispasmodics and muscle contractants, miotics and anticholinergics, anti-glaucoma compounds, anti-parasite and/or anti-protozoal compounds, anti-hypertensives, analgesics, anti-pyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, and vaccines.

Exemplary pharmaceutical agents considered to be particularly suitable for incorporation in the foams or gels used in the methods of the invention include but are not limited to imidazoles, such as miconazole, econazole, terconazole, saperconazole, itraconazole, metronidazole, fluconazole, ketoconazole, and clotrimazole, luteinizing-hormone-releasing hormone (LHRH) and its analogues, nonoxynol-9, a GnRH agonist or antagonist, natural or synthetic progestrin, such as selected progesterone, 17-hydroxyprogeterone derivatives such as medroxyprogesterone acetate, and 19-nortestosterone analogues such as norethindrone, natural or synthetic estrogens, conjugated estrogens, estradiol, estropipate, and ethinyl estradiol, bisphosphonates including etidronate, alendronate, tiludronate, resedronate, clodronate, and pamidronate, calcitonin, parathyroid hormones, carbonic anhydrase inhibitor such as felbamate and dorzolamide, a mast cell stabilizer such as xesterbergsterol-A, Iodoxamine, and cromolyn, a prostaglandin inhibitor such as diclofenac and ketorolac, a steroid such as prednisolone, dexamethasone, fluoromethylone, rimexolone, and lotepednol, an antihistamine such as antazoline, pheniramine, and histiminase, pilocarpine nitrate, a beta-blocker such as levobunolol and timolol maleate. As will be understood by those skilled in the art, two or more pharmaceutical agents may be combined for specific effects. The necessary amounts of active ingredient can be determined by simple experimentation.

By way of example only, any of a number of antibiotics and antimicrobials may be included in the foams or gels used in the methods of the invention. Antimicrobial drugs preferred for inclusion in compositions used in the methods of the invention include salts of lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole and amanfadine and the like.

By way of example only, in the case of anti-inflammation, non-steroidal anti-inflammatory agents (NSAIDS) may be incorporated in the foams or gels used in the methods of the invention, such as propionic acid derivatives, acetic acid, fenamic acid derivatives, biphenylcarboxylic acid derivatives, oxicams, including but not limited to aspirin, acetaminophen, ibuprofen, naproxen, benoxaprofen, flurbiprofen, fenbufen, ketoprofen, indoprofen, pirprofen, carporfen, and bucloxic acid and the like.

Selected Compositions of the Invention

One aspect of the invention relates to a composition comprising a biopolymer, a cross-linker, and a polymeric additive; wherein the polymeric additive accelerates a cross-linking reaction between the biopolymer and the cross-linker.

In certain embodiments, the present invention relates to the aforementioned composition, wherein said composition is a gel or foam.

In certain embodiments, the present invention relates to the aforementioned composition wherein said biopolymer contains a plurality of amine groups.

In certain embodiments, the present invention relates to the aforementioned composition, wherein said biopolymer is a protein, polysaccharide, or polynucleotide.

In certain embodiments, the present invention relates to the aforementioned composition, wherein said biopolymer is a protein.

In certain embodiments, the present invention relates to the aforementioned composition, wherein said biopolymer is a protein selected from the group consisting of actin, albumin, alpha-globulin, beta-globulin, gamma-globulin, cadherin, calmodulin, calbindin, casein, catenin, collagens, C-reactive protein, cholesterylester transfer protein, cytokines, DNA binding proteins, dystrophin, elastin, ferritin, fetuin, fibrinogen, fibrin, fibroin, fibronectin, gelatin, hemoglobin, histones, insulin, epidermal growth factor, heparin, interleukins, insulin-like growth factor, integrin, keratin, kinases, laminin, lysozyme, myoglobin, myosin, reelin, rhodopsin, selectin, transthyretin, thrombin, tubulin, trypsin, utrophin and vinculin.

In certain embodiments, the present invention relates to the aforementioned composition, wherein said biopolymer is albumin.

In certain embodiments, the present invention relates to the aforementioned composition, wherein said albumin is a mammalian albumin.

In certain embodiments, the present invention relates to the aforementioned composition, wherein said albumin is a mammalian serum albumin.

In certain embodiments, the present invention relates to the aforementioned composition, wherein said albumin is human serum albumin or bovine serum albumin.

In certain embodiments, the present invention relates to the aforementioned composition, wherein said albumin is human serum albumin.

In certain embodiments, the present invention relates to the aforementioned composition, wherein said albumin is bovine serum albumin.

In certain embodiments, the present invention relates to the aforementioned composition, wherein said albumin is not bovine serum albumin.

In certain embodiments, the present invention relates to the aforementioned composition, wherein said cross-linker is a dialdehyde or a polyaldehyde.

In certain embodiments, the present invention relates to the aforementioned composition, wherein said cross-linker is a dialdehyde.

In certain embodiments, the present invention relates to the aforementioned composition, wherein said cross-linker is W—X$_n$—W, wherein independently for each occurrence, W is

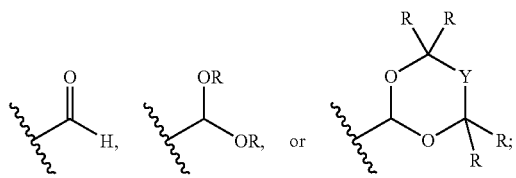

X is —C(R)$_2$—; or, for at most two, three, four, five, six, seven or eight occurrences, X is —C(═O)—, —O—, —S—, —N(R)—, —N(C(O)R)—, —C(R)═C(R)—, —C≡C—, —C≡N—, —C(R)═N—, a cycloalkyl diradical, a heterocycloalkyl diradical, an aryl diradical, or a heteroaryl diradical;

Y is a bond, —C(R)$_2$—, —C(═O)—, —O—, —S—, —N(R)—, or —N(C(O)R)—;

R is hydrogen, alkyl, lower alkyl, carbocyclyl, alkenyl, lower alkenyl, alkynyl, lower alkynyl, aryl, heteroaryl, aralkyl, or heteroaralkyl; and n is 1-20 inclusive.

In certain embodiments, the present invention relates to the aforementioned cross-linker, wherein W is

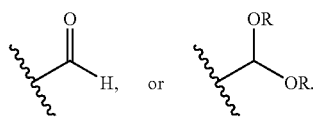

In certain embodiments, the present invention relates to the aforementioned cross-linker, wherein W is

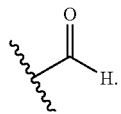

In certain embodiments, the present invention relates to the aforementioned cross-linker, wherein W is

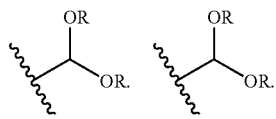

In certain embodiments, the present invention relates to the aforementioned cross-linker, wherein X is —CR$_2$—. In certain embodiments, the present invention relates to the aforementioned cross-linker, wherein X is —CH$_2$—.

In certain embodiments, the present invention relates to the aforementioned cross-linker, wherein Y is a bond, —CR$_2$—, or —O—. In certain embodiments, the present invention relates to the aforementioned cross-linker, wherein Y is a bond, or —CH$_2$—.

In certain embodiments, the present invention relates to the aforementioned cross-linker, wherein R is hydrogen or lower alkyl. In certain embodiments, the present invention relates to the aforementioned cross-linker, wherein R is hydrogen.

In certain embodiments, the present invention relates to the aforementioned cross-linker, wherein n is 1-10 inclusive. In certain embodiments, the present invention relates to the aforementioned cross-linker, wherein n is 2. In certain embodiments, the present invention relates to the aforementioned cross-linker, wherein n is 3. In certain embodiments, the present invention relates to the aforementioned cross-linker, wherein n is 4. In certain embodiments, the present invention relates to the aforementioned cross-linker, wherein n is 5. In certain embodiments, the present invention relates to the aforementioned cross-linker, wherein n is 6.

In certain embodiments, the present invention relates to the aforementioned composition, wherein said cross-linker is glutaraldehyde.

In certain embodiments, the present invention relates to the aforementioned composition, wherein said cross-linker is not glutaraldehyde.

In certain embodiments, the present invention relates to the aforementioned composition, wherein said crosslinker is represented by the following formula:

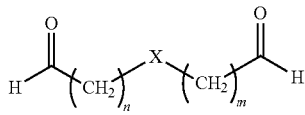

wherein independently for each occurrence
n is 0-12;
m is 0-12; and
X is a di-radical of an aliphatic, cycloaliphatic, aromatic, heterocycloaliphatic or heterocyclic moiety.

In certain embodiments, the present invention relates to the aforementioned composition, wherein said crosslinker of the invention is represented by the following formula:

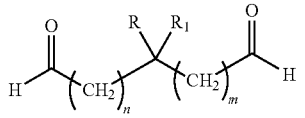

wherein independently for each occurrence
n is 0-12;
m is 0-12; and
R and $R_1$ are each independently hydrogen, aliphatic, cycloaliphatic, aromatic, heterocycloaliphatic or heterocyclic moiety.

In certain embodiments, the present invention relates to the aforementioned composition, wherein said cross-linker is water soluble at a concentration of at least about 1 mg/mL.

In certain embodiments, the present invention relates to the aforementioned composition, wherein said cross-linker is water soluble at a concentration of at least about 2.5 mg/mL.

In certain embodiments, the present invention relates to the aforementioned composition, wherein said cross-linker is water soluble at a concentration of at least about 5 mg/mL.

In certain embodiments, the present invention relates to the aforementioned composition, wherein said cross-linker is water soluble at a concentration of at least about 10 mg/mL.

In certain embodiments, the present invention relates to the aforementioned composition, wherein said cross-linker is water soluble at a concentration of at least about 20 mg/mL.

In certain embodiments, the present invention relates to the aforementioned composition, wherein said biopolymer is a mammalian serum albumin; and the cross-linker is glutaraldehyde.

In certain embodiments, the present invention relates to the aforementioned composition, wherein said biopolymer is human serum albumin or bovine serum albumin; and the cross-linker is glutaraldehyde.

In certain embodiments, the present invention relates to the aforementioned composition, wherein the weight ratio of biopolymer to cross-linker is about 30:1 to about 200:1.

In certain embodiments, the present invention relates to the aforementioned composition, wherein the weight ratio of biopolymer to cross-linker is about 60:1 to about 120:1.

In certain embodiments, the present invention relates to the aforementioned composition, wherein the weight ratio of biopolymer to cross-linker is about 80:1 to about 120:1.

In certain embodiments, the present invention relates to the aforementioned composition, wherein the weight ratio of biopolymer to cross-linker is about 100:1 to about 120:1.

In certain embodiments, the present invention relates to the aforementioned composition, wherein the weight ratio of biopolymer to cross-linker is about 80:1 to about 100:1.

In certain embodiments, the present invention relates to the aforementioned composition, wherein said polymeric additive accelerates Schiff base formation.

In certain embodiments, the present invention relates to the aforementioned composition, wherein said polymeric additive is a poly(vinylpyrrolidone) polymer or copolymer, dextran, a poly(ethylene glycol) or a carbomer.

In certain embodiments, the present invention relates to the aforementioned composition, wherein said polymeric additive is a poly(vinylpyrrolidone) or dextran.

In certain embodiments, the present invention relates to the aforementioned composition, wherein said composition further comprises a gas.

In certain embodiments, the present invention relates to the aforementioned composition, wherein said gas is non-toxic.

In certain embodiments, the present invention relates to the aforementioned composition, wherein said gas is oxygen or air.

In certain embodiments, the present invention relates to the aforementioned composition, wherein said polymeric additive has a weight average molecular weight of between about 25,000 g/mol and about 250,000 g/mol.

In certain embodiments, the present invention relates to the aforementioned composition, wherein said polymeric additive has a weight average molecular weight of between about 25,000 g/mol and about 150,000 g/mol.

In certain embodiments, the present invention relates to the aforementioned composition, wherein said polymeric additive has a weight average molecular weight of about 50,000 g/mol.

In certain embodiments, the present invention relates to the aforementioned composition, further comprising a foam-modifying agent.

In certain embodiments, the present invention relates to the aforementioned composition, wherein said foam-modifying agent is a surfactant.

In certain embodiments, the present invention relates to the aforementioned composition, wherein said foam-modifying agent is tyloxapol, a poloxamer, a poloxamine, a phospholipid, or glycerol.

In certain embodiments, the present invention relates to the aforementioned composition, further comprising an anti-infective.

In certain embodiments, the present invention relates to the aforementioned composition, wherein said anti-infective is selected from the group consisting of an aminoglycoside, a tetracycline, a sulfonamide, p-aminobenzoic acid, a diaminopyrimidine, a quinolone, a β-lactam, a β-lactamase inhibitor, chloraphenicol, a macrolide, penicillins, cephalosporins, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, and terbinafine, or a combination thereof.

In certain embodiments, the present invention relates to the aforementioned composition, wherein said anti-infective is tetracycline.

In certain embodiments, the present invention relates to the aforementioned composition, further comprising a contrast-enhancing agent.

In certain embodiments, the present invention relates to the aforementioned composition, wherein said contrast-enhancing agent is selected from the group consisting of radiopaque materials, paramagnetic materials, heavy atoms, transition metals, lanthanides, actinides, dyes, and radionuclide-containing materials.

In certain embodiments, the present invention relates to the aforementioned composition, wherein upon combination of said biopolymer; said cross-linker; and said polymeric additive, said biopolymer and said cross-linker are substantially cross-linked in about 1 minute to about 10 minutes.

In certain embodiments, the present invention relates to the aforementioned composition, wherein upon combination of said biopolymer; said cross-linker; and said polymeric additive, said biopolymer and said cross-linker are substantially cross-linked in about 1 minute to about 7 minutes.

In certain embodiments, the present invention relates to the aforementioned composition, wherein upon combination of said biopolymer; said cross-linker; and said polymeric additive, said biopolymer and said cross-linker are substantially cross-linked in about 1 minute to about 5 minutes.

In certain embodiments, the present invention relates to the aforementioned composition, wherein upon combination of said biopolymer; said cross-linker; and said polymeric additive, said biopolymer and said cross-linker are substantially cross-linked in about 2 minutes to about 6 minutes.

In certain embodiments, the present invention relates to the aforementioned composition, wherein upon combination of said biopolymer; said cross-linker; and said polymeric additive, said biopolymer and said cross-linker are substantially cross-linked in about 3 minutes to about 5 minutes.

In certain embodiments, the present invention relates to the aforementioned composition, wherein said composition substantially degrades under physiological conditions in about 1 to about 12 weeks.

In certain embodiments, the present invention relates to the aforementioned composition, wherein said composition substantially degrades under physiological conditions in about 1 to about 6 weeks.

In certain embodiments, the present invention relates to the aforementioned composition, wherein said composition substantially degrades under physiological conditions in about 1 to about 4 weeks.

In certain embodiments, the present invention relates to the aforementioned composition, wherein said composition substantially degrades under physiological conditions in about 2 to about 5 weeks.

In certain embodiments, the present invention relates to the aforementioned composition, wherein said composition is in contact with a mammalian tissue.

In certain embodiments, the present invention relates to the aforementioned composition, wherein said composition is in contact with a mammalian pulmonary tissue.

In certain embodiments, the present invention relates to the aforementioned composition, wherein said composition contacts an interior surface of a mammalian pulmonary tissue.

In certain embodiments, the present invention relates to the aforementioned composition, wherein said composition contacts the interior surface of mammalian alveoli.

In certain embodiments, the present invention relates to the aforementioned composition, wherein said composition contacts the interior surface of mammalian alveoli and partially or completely fills the mammalian alveoli.

Selected Methods of the Invention

Aspects of the invention relate to certain formulations of compositions that are useful for non-surgical lung volume reduction. According to the invention, lung volume reduction, a procedure that reduces lung size by removing damaged (e.g., over-expanded) regions of the lung, can be accomplished non-surgically by procedures carried out through the patient's trachea (e.g., by inserting devices and substances through a bronchoscope), rather than by procedures that disrupt the integrity of the chest wall [Ingenito et al., *Am. J. Resp. Crit. Care Med.* 2001, 164, 295-301; Ingenito et al., *Am. J. Resp. Crit. Care Med.* 2000, 161, A750; and Ingenito et al., *Am J. Resp. Crit. Care Med.* 2001, 163, A957.] In one aspect of the invention, non-surgical lung volume reduction is performed by introducing a material (e.g., a biopolymer foam or gel) into a target region of the lung to promote collapse of the target region. In one embodiment, the material promotes stable collapse by adhering to the collapsed tissue together and/or by promoting scarring of the collapsed tissue.

Once a patient is determined to be a candidate for LVR, the target region of the lung can be identified using radiological studies (e.g., chest X-rays) and computed tomography scans. When the LVR procedure is subsequently performed, the patient is anesthetized and intubated, and can be placed on an absorbable gas (e.g., at least 90% oxygen and up to 100% oxygen) for a specified period of time (e.g., approximately 30 minutes). The region(s) of the lung that were first identified radiologically are then identified bronchoscopically.

Suitable bronchoscopes include those manufactured by Pentax, Olympus, and Fujinon, which allow for visualization of an illuminated field. The physician guides the bronchoscope into the trachea and through the bronchial tree so that the open tip of the bronchoscope is positioned at the entrance to target region (i.e., to the region of the lung that will be reduced in volume). The bronchoscope can be guided through progressively narrower branches of the bronchial tree to reach various subsegments of either lung. For example, the bronchoscope can be guided to a subsegment within the upper lobe of the patient's left lung.

In certain embodiments, a balloon catheter may be guided through the bronchoscope to a target region of the lung. When the catheter is positioned within the bronchoscope, the balloon is inflated so that material passed through the catheter will be contained in regions of the lung distal to the balloon. This is particularly may be useful in the methods of the present invention, which include the introduction of compositions of the invention into the selected region of the lung. The balloon (or balloon-like structure) may be spherical, cylindrical, or any other shape. The distended balloon (or balloon-like structure) may have a diameter of at least about 0.1 mm, at least about 0.5 mm, at least about 1.0 mm, at least about 1.5 mm, at least about 3 mm, at least about 4 mm, at least about 5 mm, at least about 6 mm, at least about 7 mm, at least about 8 mm, at least about 9 mm, or at least about 10 mm. The balloon diameter may be less than about 30 mm, less than about 20 mm, less than about 15 mm, or less than about 12 mm. The diameter selected can help position the balloon (or balloon-like structure) in a segmental bronchi, subsegmental bronchi, bronchiole and/or alveolus within a deep region of the lung. This anchoring and/or positioning can facilitate delivery of a composition of the present invention to the selected localized region of damaged lung tissue.

One aspect of the invention relates to a method for reducing lung volume in a patient by administering, a composition comprising a biopolymer, a cross-linker, and a polymeric additive; wherein said polymeric additive accelerates a cross-linking reaction between the biopolymer and the cross-linker.

In certain embodiments, the method further comprises the step of advancing into a region of a patient's lung via said patient's trachea a catheter lumen through a bronchoscope.

In certain embodiments, the composition further comprises a gas.

In certain embodiments, the present invention relates to the aforementioned method, wherein said gas is non-toxic.

In certain embodiments, the present invention relates to the aforementioned method, wherein said gas is oxygen or air.

In certain embodiments, the components of the composition are preferably mixed together shortly before application. This mixing can take place for example with the aid of a double-barrel syringe in which the components are forced into a joint ejection tube in which a static mixer is present. The components are mixed together by the static mixer in the ejection tube and are ejected, before substantial cross-linking has occurred, from the syringe onto the catheter.

For example, in certain embodiments, the present invention relates to the aforementioned method, further comprising the step of preparing a foam composition by using a gas to foam a mixture of a biopolymer, a cross-linker, and a polymeric additive; wherein the polymeric additive accelerates a cross-linking reaction between the biopolymer and the cross-linker.

In other embodiments, the present invention relates to the aforementioned method, further comprising the steps of using a gas to foam a mixture of a biopolymer, and a polymeric additive, thereby forming a foamed mixture; and then preparing a foam composition by adding a cross-linker to the foamed mixture; wherein the polymeric additive accelerates a cross-linking reaction between the biopolymer and the cross-linker. In certain embodiments, the present invention relates to the aforementioned method, wherein said method results in the deflation and atelectasis of said region of the lung.

In certain embodiments, the present invention relates to the aforementioned method, wherein said region of the lung has little or no physiological function.

In certain embodiments, the present invention relates to the aforementioned method wherein said biopolymer contains a plurality of amine groups.

In certain embodiments, the present invention relates to the aforementioned method, wherein said biopolymer is a protein, polysaccharide, or polynucleotide.

In certain embodiments, the present invention relates to the aforementioned method, wherein said biopolymer is a protein.

In certain embodiments, the present invention relates to the aforementioned method, wherein said biopolymer is a protein selected from the group consisting of actin, albumin, alpha-globulin, beta-globulin, gamma-globulin, cadherin, calmodulin, calbindin, casein, catenin, collagens, C-reactive protein, cholesterylester transfer protein, cytokines, DNA binding proteins, dystrophin, elastin, ferritin, fetuin, fibrinogen, fibrin, fibroin, fibronectin, gelatin, hemoglobin, histones, insulin, epidermal growth factor, heparin, interleukins, insulin-like growth factor, integrin, keratin, kinases, laminin, lysozyme, myoglobin, myosin, reelin, rhodopsin, selectin, transthyretin, thrombin, tubulin, trypsin, utrophin and vinculin.

In certain embodiments, the present invention relates to the aforementioned method, wherein said biopolymer is albumin.

In certain embodiments, the present invention relates to the aforementioned method, wherein said albumin is a mammalian albumin.

In certain embodiments, the present invention relates to the aforementioned method, wherein said albumin is a mammalian serum albumin.

In certain embodiments, the present invention relates to the aforementioned method, wherein said albumin is human serum albumin or bovine serum albumin.

In certain embodiments, the present invention relates to the aforementioned method, wherein said albumin is human serum albumin.

In certain embodiments, the present invention relates to the aforementioned method, wherein said albumin is bovine serum albumin.

In certain embodiments, the present invention relates to the aforementioned method, wherein said albumin is not bovine serum albumin.

In certain embodiments, the present invention relates to the aforementioned method, wherein said cross-linker is a dialdehyde or a polyaldehyde.

In certain embodiments, the present invention relates to the aforementioned method, wherein said cross-linker is a dialdehyde.

In certain embodiments, the present invention relates to the aforementioned method, wherein said cross-linker is W—$X_n$—W, wherein independently for each occurrence, W is

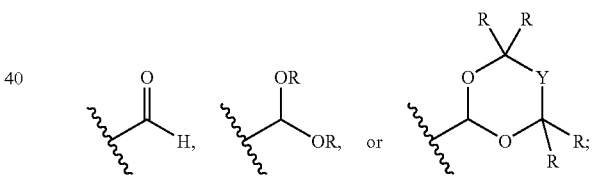

X is —$C(R)_2$—; or, for at most two, three, four, five, six, seven or eight occurrences, X is —C(=O)—, —O—, —S—, —N(R)—, —N(C(O)R)—, —C(R)=C(R)—, —C≡C—, —C≡N—, —C(R)=N—, a cycloalkyl diradical, a heterocycloalkyl diradical, an aryl diradical, or a heteroaryl diradical;

Y is a bond, —$C(R)_2$—, —C(=O)—, —O—, —S—, —N(R)—, or —N(C(O)R)—;

R is hydrogen, alkyl, lower alkyl, carbocyclyl, alkenyl, lower alkenyl, alkynyl, lower alkynyl, aryl, heteroaryl, aralkyl, or heteroaralkyl; and n is 1-20 inclusive.

In certain embodiments, the present invention relates to the aforementioned method, wherein W is

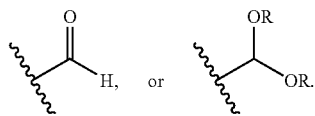

In certain embodiments, the present invention relates to the aforementioned method, wherein W is

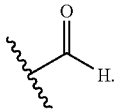

In certain embodiments, the present invention relates to the aforementioned method, wherein W is

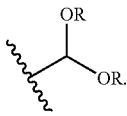

In certain embodiments, the present invention relates to the aforementioned method, wherein X is —CR$_2$—. In certain embodiments, the present invention relates to the aforementioned method, wherein X is —CH$_2$—.

In certain embodiments, the present invention relates to the aforementioned method, wherein Y is a bond, —CR$_2$—, or —O—. In certain embodiments, the present invention relates to the aforementioned method, wherein Y is a bond, or —CH$_2$—.

In certain embodiments, the present invention relates to the aforementioned method, wherein R is hydrogen or lower alkyl. In certain embodiments, the present invention relates to the aforementioned method, wherein R is hydrogen.

In certain embodiments, the present invention relates to the aforementioned method, wherein n is 1-10 inclusive. In certain embodiments, the present invention relates to the aforementioned method, wherein n is 2. In certain embodiments, the present invention relates to the aforementioned method, wherein n is 3. In certain embodiments, the present invention relates to the aforementioned method, wherein n is 4. In certain embodiments, the present invention relates to the aforementioned method, wherein n is 5. In certain embodiments, the present invention relates to the aforementioned method, wherein n is 6.

In certain embodiments, the present invention relates to the aforementioned method, wherein said cross-linker is glutaraldehyde.

In certain embodiments, the present invention relates to the aforementioned method, wherein said cross-linker is not glutaraldehyde.

In certain embodiments, the present invention relates to the aforementioned method, wherein said cross-linker is represented by the following formula:

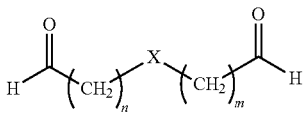

wherein independently for each occurrence
n is 0-12;
m is 0-12; and
X is a di-radical of an aliphatic, cycloaliphatic, aromatic, heterocycloaliphatic or heterocyclic moiety.

In certain embodiments, the present invention relates to the aforementioned method, wherein said cross-linker is represented by the following formula:

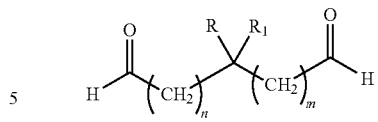

wherein independently for each occurrence
n is 0-12;
m is 0-12; and
R and R$_1$ are each independently hydrogen, aliphatic, cycloaliphatic, aromatic, heterocycloaliphatic or heterocyclic moiety.

In certain embodiments, the present invention relates to the aforementioned method, wherein said cross-linker is water soluble at a concentration of at least about 1 mg/mL.

In certain embodiments, the present invention relates to the aforementioned method, wherein said cross-linker is water soluble at a concentration of at least about 2.5 mg/mL.

In certain embodiments, the present invention relates to the aforementioned method, wherein said cross-linker is water soluble at a concentration of at least about 5 mg/mL.

In certain embodiments, the present invention relates to the aforementioned method, wherein said cross-linker is water soluble at a concentration of at least about 10 mg/mL.

In certain embodiments, the present invention relates to the aforementioned method, wherein said cross-linker is water soluble at a concentration of at least about 20 mg/mL.

In certain embodiments, the present invention relates to the aforementioned method, wherein said biopolymer is a mammalian serum albumin; and the cross-linker is glutaraldehyde.

In certain embodiments, the present invention relates to the aforementioned method, wherein said biopolymer is human serum albumin or bovine serum albumin; and the cross-linker is glutaraldehyde.

In certain embodiments, the present invention relates to the aforementioned method, wherein the weight ratio of biopolymer to cross-linker is about 30:1 to about 200:1.

In certain embodiments, the present invention relates to the aforementioned method, wherein the weight ratio of biopolymer to cross-linker is about 60:1 to about 120:1.

In certain embodiments, the present invention relates to the aforementioned method, wherein the weight ratio of biopolymer to cross-linker is about 80:1 to about 120:1.

In certain embodiments, the present invention relates to the aforementioned method, wherein the weight ratio of biopolymer to cross-linker is about 100:1 to about 120:1.

In certain embodiments, the present invention relates to the aforementioned method, wherein the weight ratio of biopolymer to cross-linker is about 80:1 to about 100:1.

In certain embodiments, the present invention relates to the aforementioned method, wherein said polymeric additive accelerates Schiff base formation.

In certain embodiments, the present invention relates to the aforementioned method, wherein said polymeric additive is a poly(vinylpyrrolidone) polymer or copolymer, dextran, a poly(ethylene glycol) or a carbomer.

In certain embodiments, the present invention relates to the aforementioned method, wherein said polymeric additive is a poly(vinylpyrrolidone) or dextran.

In certain embodiments, the present invention relates to the aforementioned method, wherein said polymeric additive has a weight average molecular weight of between about 25,000 g/mol and about 250,000 g/mol.

In certain embodiments, the present invention relates to the aforementioned method, wherein said polymeric additive has a weight average molecular weight of between about 25,000 g/mol and about 150,000 g/mol.

In certain embodiments, the present invention relates to the aforementioned method, wherein said polymeric additive has a weight average molecular weight of about 50,000 g/mol.

In certain embodiments, the present invention relates to the aforementioned method, wherein said composition further comprises a foam-modifying agent.

In certain embodiments, the present invention relates to the aforementioned method, wherein said foam-modifying agent is a surfactant.

In certain embodiments, the present invention relates to the aforementioned method, wherein said foam-modifying agent is tyloxapol, a poloxamer, a poloxamine, a phospholipid, or glycerol.

In certain embodiments, the present invention relates to the aforementioned method, wherein said composition further comprises an anti-infective.

In certain embodiments, the present invention relates to the aforementioned method, wherein said anti-infective is selected from the group consisting of an aminoglycoside, a tetracycline, a sulfonamide, p-aminobenzoic acid, a diaminopyrimidine, a quinolone, a β-lactam, a β-lactamase inhibitor, chloraphenicol, a macrolide, penicillins, cephalosporins, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, and terbinafine, or a combination thereof.

In certain embodiments, the present invention relates to the aforementioned method, wherein said anti-infective is tetracycline.

In certain embodiments, the present invention relates to the aforementioned method, wherein said composition further comprises a contrast-enhancing agent.

In certain embodiments, the present invention relates to the aforementioned method, wherein said contrast-enhancing agent is selected from the group consisting of radiopaque materials, paramagnetic materials, heavy atoms, transition metals, lanthanides, actinides, dyes, and radionuclide-containing materials.

In certain embodiments, the present invention relates to the aforementioned method, wherein the total amount of the composition is between about 5 mL and about 300 mL.

In certain embodiments, the present invention relates to the aforementioned method, wherein the total amount of the composition is between about 10 mL and about 100 mL.

In certain embodiments, the present invention relates to the aforementioned method, wherein the total amount of the composition is between about 10 mL and about 50 mL.

In certain embodiments, the present invention relates to the aforementioned method, wherein upon combination of said albumin; said cross-linker; and said polymeric additive, said biopolymer and said cross-linker are substantially cross-linked in about 1 minute to about 10 minutes.

In certain embodiments, the present invention relates to the aforementioned method, wherein upon combination of said albumin; said cross-linker; and said polymeric additive, said biopolymer and said cross-linker are substantially cross-linked in about 1 minute to about 7 minutes.

In certain embodiments, the present invention relates to the aforementioned method, wherein upon combination of said albumin; said cross-linker; and said polymeric additive, said biopolymer and said cross-linker are substantially cross-linked in about 1 minute to about 5 minutes.

In certain embodiments, the present invention relates to the aforementioned method, wherein upon combination of said albumin; said cross-linker; and said polymeric additive, said biopolymer and said cross-linker are substantially cross-linked in about 2 minutes to about 6 minutes.

In certain embodiments, the present invention relates to the aforementioned method, wherein upon combination of said albumin; said cross-linker; and said polymeric additive, said biopolymer and said cross-linker are substantially cross-linked in about 3 minutes to about 5 minutes.

In certain embodiments, the present invention relates to the aforementioned method, wherein said composition substantially degrades under physiological conditions in about 1 to about 12 weeks.

In certain embodiments, the present invention relates to the aforementioned method, wherein said composition substantially degrades under physiological conditions in about 1 to about 6 weeks.

In certain embodiments, the present invention relates to the aforementioned method, wherein said composition substantially degrades under physiological conditions in about 1 to about 4 weeks.

In certain embodiments, the present invention relates to the aforementioned method, wherein said composition substantially degrades under physiological conditions in about 2 to about 5 weeks.

In certain embodiments, the present invention relates to the aforementioned method, wherein said patient is a human.

In certain embodiments, the present invention relates to the aforementioned method, wherein said patient has emphysema.

In certain embodiments, the present invention relates to the aforementioned method, wherein said patient has suffered a traumatic injury of the lung.

In certain embodiments, the present invention relates to the aforementioned method, further comprising the step of collapsing the region of the lung.

In certain embodiments, the present invention relates to the aforementioned method, wherein said composition is in contact with a mammalian tissue.

In certain embodiments, the present invention relates to the aforementioned method, wherein said foam composition is in contact with a mammalian pulmonary tissue.

In certain embodiments, the present invention relates to the aforementioned method, wherein said foam composition contacts an interior surface of a mammalian pulmonary tissue.

In certain embodiments, the present invention relates to the aforementioned method, wherein said foam composition contacts the interior surface of mammalian alveoli.

In certain embodiments, the present invention relates to the aforementioned method, wherein said foam composition contacts the interior surface of mammalian alveoli and partially or completely fills the mammalian alveoli.

Selected Kits of the Invention

This invention also provides kits for conveniently and effectively implementing the methods of this invention. Such kits comprise any of the biopolymers, polymeric additives, and/or cross-linkers of the present invention or a combination thereof, and a means for facilitating their use consistent with methods of this invention. Such kits provide a convenient and effective means for assuring that the methods are practiced in an effective manner. The compliance means of such kits includes any means which facilitates practicing a method of this invention. Such compliance means include instructions, packaging, and dispensing means, and combinations thereof. Kit components may be packaged for either manual or partially or wholly automated practice of the foregoing methods. In other embodiments, this invention contemplates a kit including albumins and/or cross-linkers of the present invention, and optionally instructions for their use.

Any of these kits can contain devices used in non-surgical lung volume reduction. For example, they can also contain a catheter (e.g., a single- or multi-lumen (e.g., dual-lumen) catheter that, optionally, includes a balloon or other device suitable for inhibiting airflow within the respiratory tract), tubing or other conduits for removing material (e.g., solutions, including those that carry debrided epithelial cells) from the lung, a stent or a valve or other device that may be placed in an airway to block or reduce airflow into or out of a lung or lung region, and/or a bronchoscope.

One aspect of the invention relates to a kit, comprising: a first container comprising a first amount of a first mixture comprising a biopolymer; a second container comprising a second amount of a second mixture comprising a cross-linker; a third container comprising a third amount of a third mixture comprising a polymeric additive which modifies the rate of cross-linking; and instructions for use in lung volume reduction therapy.

Another aspect of the invention relates to a kit, comprising: a first container comprising a first amount of a first mixture comprising an albumin; a second container comprising a second amount of a second mixture comprising a cross-linker; a third container comprising a third amount of a third mixture comprising a polymeric additive; and instructions for use in lung volume reduction therapy.

In certain embodiments, the present invention relates to the aforementioned kit, wherein the total amount of the first mixture, second mixture, and third mixture is between about 5 mL and about 300 mL.

In certain embodiments, the present invention relates to the aforementioned kit, wherein the total amount of the first mixture, second mixture, and third mixture is between about 10 mL and about 100 mL.

In certain embodiments, the present invention relates to the aforementioned kit, wherein the total amount of the first mixture, second mixture and third mixture is between about 10 mL and about 50 mL.

In certain embodiments, the present invention relates to the aforementioned kit, wherein said biopolymer contains a plurality of amine groups.

In certain embodiments, the present invention relates to the aforementioned kit, wherein said biopolymer is a protein, polysaccharide, or polynucleotide.

In certain embodiments, the present invention relates to the aforementioned kit, wherein said biopolymer is a protein.

In certain embodiments, the present invention relates to the aforementioned kit, wherein said biopolymer is a protein selected from the group consisting of actin, albumin, alpha-globulin, beta-globulin, gamma-globulin, cadherin, calmodulin, calbindin, casein, catenin, collagens, C-reactive protein, cholesterylester transfer protein, cytokines, DNA binding proteins, dystrophin, elastin, ferritin, fetuin, fibrinogen, fibrin, fibroin, fibronectin, gelatin, hemoglobin, histones, insulin, epidermal growth factor, heparin, interleukins, insulin-like growth factor, integrin, keratin, kinases, laminin, lysozyme, myoglobin, myosin, reelin, rhodopsin, selectin, transthyretin, thrombin, tubulin, trypsin, utrophin and vinculin.

In certain embodiments, the present invention relates to the aforementioned kit, wherein said protein is albumin.

In certain embodiments, the present invention relates to the aforementioned kit, wherein said albumin is a mammalian albumin.

In certain embodiments, the present invention relates to the aforementioned kit, wherein said albumin is a mammalian serum albumin.

In certain embodiments, the present invention relates to the aforementioned kit, wherein said albumin is human serum albumin or bovine serum albumin.

In certain embodiments, the present invention relates to the aforementioned kit, wherein said albumin is human serum albumin.

In certain embodiments, the present invention relates to the aforementioned kit, wherein said albumin is bovine serum albumin.

In certain embodiments, the present invention relates to the aforementioned kit, wherein said albumin is not bovine serum albumin.

In certain embodiments, the present invention relates to the aforementioned kit, wherein said cross-linker is a dialdehyde or a polyaldehyde.

In certain embodiments, the present invention relates to the aforementioned kit, wherein said cross-linker is a dialdehyde.

In certain embodiments, the present invention relates to the aforementioned kit, wherein said cross-linker is W—$X_n$—W, wherein independently for each occurrence, W is

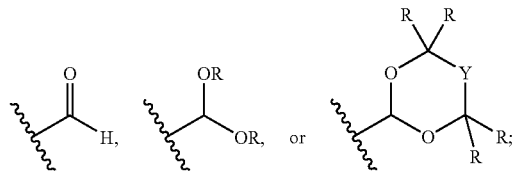

X is —C(R)$_2$—; or, for at most two, three, four, five, six, seven or eight occurrences, X is —C(=O)—, —O—, —S—, —N(R)—, —N(C(O)R)—, —C(R)=C(R)—, —C≡C—, —C≡N—, —C(R)=N—, a cycloalkyl diradical, a heterocycloalkyl diradical, an aryl diradical, or a heteroaryl diradical;

Y is a bond, —C(R)$_2$—, —C(=O)—, —O—, —S—, —N(R)—, or —N(C(O)R)—;

R is hydrogen, alkyl, lower alkyl, carbocyclyl, alkenyl, lower alkenyl, alkynyl, lower alkynyl, aryl, heteroaryl, aralkyl, or heteroaralkyl; and n is 1-20 inclusive.

In certain embodiments, the present invention relates to the aforementioned kit, wherein W is

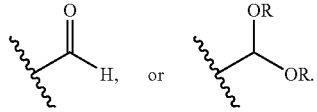

In certain embodiments, the present invention relates to the aforementioned kit, wherein W is

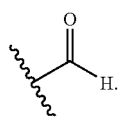

In certain embodiments, the present invention relates to the aforementioned kit, wherein W is

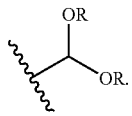

In certain embodiments, the present invention relates to the aforementioned kit, wherein X is —CR$_2$—. In certain embodiments, the present invention relates to the aforementioned kit, wherein X is —CH$_2$—.

In certain embodiments, the present invention relates to the aforementioned kit, wherein Y is a bond, —CR$_2$—, or —O—. In certain embodiments, the present invention relates to the aforementioned kit, wherein Y is a bond, or —CH$_2$—.

In certain embodiments, the present invention relates to the aforementioned kit, wherein R is hydrogen or lower alkyl. In certain embodiments, the present invention relates to the aforementioned kit, wherein R is hydrogen.

In certain embodiments, the present invention relates to the aforementioned kit, wherein n is 1-10 inclusive. In certain embodiments, the present invention relates to the aforementioned kit, wherein n is 2. In certain embodiments, the present invention relates to the aforementioned kit, wherein n is 3. In certain embodiments, the present invention relates to the aforementioned kit, wherein n is 4. In certain embodiments, the present invention relates to the aforementioned kit, wherein n is 5. In certain embodiments, the present invention relates to the aforementioned kit, wherein n is 6.

In certain embodiments, the present invention relates to the aforementioned kit, wherein said cross-linker is glutaraldehyde.

In certain embodiments, the present invention relates to the aforementioned kit, wherein said cross-linker is not glutaraldehyde.

In certain embodiments, the present invention relates to the aforementioned kit, wherein said crosslinker is represented by the following formula:

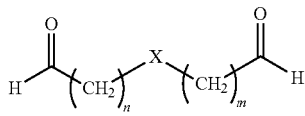

wherein independently for each occurrence
n is 0-12;
m is 0-12; and
X is a di-radical of an aliphatic, cycloaliphatic, aromatic, heterocycloaliphatic or heterocyclic moiety.

In certain embodiments, the present invention relates to the aforementioned kit, wherein said crosslinker is represented by the following formula:

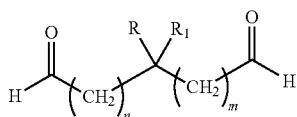

wherein independently for each occurrence
n is 0-12;
m is 0-12; and

R and R$_1$ are each independently hydrogen, aliphatic, cycloaliphatic, aromatic, heterocycloaliphatic or heterocyclic moiety.

In certain embodiments, the present invention relates to the aforementioned kit, wherein said polymeric additive accelerates Schiff base formation.

In certain embodiments, the present invention relates to the aforementioned kit, wherein said polymeric additive is a poly(vinylpyrrolidone) polymer or copolymer, dextran, a poly(ethylene glycol) or a carbomer.

In certain embodiments, the present invention relates to the aforementioned kit, wherein said polymeric additive is a poly(vinylpyrrolidone) or dextran.

In certain embodiments, the present invention relates to the aforementioned kit, wherein said cross-linker is water soluble at a concentration of at least about 1 mg/mL.

In certain embodiments, the present invention relates to the aforementioned kit, wherein said cross-linker is water soluble at a concentration of at least about 2.5 mg/mL.

In certain embodiments, the present invention relates to the aforementioned kit, wherein said cross-linker is water soluble at a concentration of at least about 5 mg/mL.

In certain embodiments, the present invention relates to the aforementioned kit, wherein said cross-linker is water soluble at a concentration of at least about 10 mg/mL.

In certain embodiments, the present invention relates to the aforementioned kit, wherein said cross-linker is water soluble at a concentration of at least about 20 mg/mL.

In certain embodiments, the present invention relates to the aforementioned kit, wherein said polymeric additive has a weight average molecular weight of between about 25,000 g/mol and about 250,000 g/mol.

In certain embodiments, the present invention relates to the aforementioned kit, wherein said polymeric additive has a weight average molecular weight of between about 25,000 g/mol and about 150,000 g/mol.

In certain embodiments, the present invention relates to the aforementioned kit, wherein said polymeric additive has a weight average molecular weight of about 50,000 g/mol.

In certain embodiments, the present invention relates to the aforementioned kit, wherein said biopolymer is albumin; said polymeric additive is poly(vinylpyrrolidone) or dextran; and the cross-linker is glutaraldehyde.

In certain embodiments, the present invention relates to the aforementioned kit, wherein said albumin is a mammalian serum albumin; said polymeric additive is poly(vinylpyrrolidone) or dextran; and the cross-linker is glutaraldehyde.

In certain embodiments, the present invention relates to the aforementioned kit, wherein said albumin is human serum albumin or bovine serum albumin; said polymeric additive is poly(vinylpyrrolidone) or dextran; and the cross-linker is glutaraldehyde.

In certain embodiments, the present invention relates to the aforementioned kit, wherein the weight ratio of biopolymer to cross-linker is about 30:1 to about 200:1.

In certain embodiments, the present invention relates to the aforementioned kit, wherein the weight ratio of biopolymer to cross-linker is about 60:1 to about 120:1.

In certain embodiments, the present invention relates to the aforementioned kit, wherein the weight ratio of biopolymer to cross-linker is about 80:1 to about 120:1.

In certain embodiments, the present invention relates to the aforementioned kit, wherein the weight ratio of biopolymer to cross-linker is about 100:1 to about 120:1.

In certain embodiments, the present invention relates to the aforementioned kit, wherein the weight ratio of biopolymer to cross-linker is about 80:1 to about 100:1.

In certain embodiments, the present invention relates to the aforementioned kit, further comprising a fourth amount of a foam-modifying agent.

In certain embodiments, the present invention relates to the aforementioned kit, wherein said foam-modifying agent is a surfactant.

In certain embodiments, the present invention relates to the aforementioned kit, wherein said foam-modifying agent is tyloxapol, a poloxamer, a poloxamine, a phospholipid, or glycerol.

In certain embodiments, the present invention relates to the aforementioned kit, further comprising a fifth amount of an anti-infective.

In certain embodiments, the present invention relates to the aforementioned kit, wherein said anti-infective is selected from the group consisting of an aminoglycoside, a tetracycline, a sulfonamide, p-aminobenzoic acid, a diaminopyrimidine, a quinolone, a β-lactam, a β-lactamase inhibitor, chloraphenicol, a macrolide, penicillins, cephalosporins, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, and terbinafine, or a combination thereof.

In certain embodiments, the present invention relates to the aforementioned kit, wherein said anti-infective is tetracycline.

In certain embodiments, the present invention relates to the aforementioned kit, further comprising a sixth amount of a contrast-enhancing agent.

In certain embodiments, the present invention relates to the aforementioned kit, wherein said contrast-enhancing agent is selected from the group consisting of radiopaque materials, paramagnetic materials, heavy atoms, transition metals, lanthanides, actinides, dyes, and radionuclide-containing materials.

In certain embodiments, the present invention relates to the aforementioned kit, wherein upon combination of said biopolymer, said cross-linker and said polymeric additive, said biopolymer and said cross-linker are substantially cross-linked in about 1 minute to about 10 minutes.

In certain embodiments, the present invention relates to the aforementioned kit, wherein upon combination of said biopolymer, said cross-linker and said polymeric additive, said biopolymer and said cross-linker are substantially cross-linked in about 1 minute to about 7 minutes.

In certain embodiments, the present invention relates to the aforementioned kit, wherein upon combination of said biopolymer, said cross-linker and said polymeric additive, said biopolymer and said cross-linker are substantially cross-linked in about 1 minute to about 5 minutes.

In certain embodiments, the present invention relates to the aforementioned kit, wherein upon combination of said biopolymer said cross-linker and said polymeric additive, said biopolymer and said cross-linker are substantially cross-linked in about 2 minutes to about 6 minutes.

In certain embodiments, the present invention relates to the aforementioned kit, wherein upon combination of said biopolymer said cross-linker and said polymeric additive, said biopolymer and said cross-linker are substantially cross-linked in about 3 minutes to about 5 minutes.

Therapeutic Applications

In addition to being useful for treating emphysema (e.g., as described above and in the following examples), compositions of the invention may be useful in other therapeutic indications.

Aspects of the invention may be used to treat any form of abnormal cellular growth (e.g., tumors, cancers, etc.) by targeting a non-toxic, yet therapeutically effective, composition to an area of diseased tissue (e.g., a tumor, adenoma, cancer, precancer, or other abnormal lesion).

Another aspect of the invention involves the use of biopolymer compositions to treat solid organ cancer. Examples of such cancers include, but are not limited to, bronchogenic carcinoma, malignant mesothelioma. Biopolymer compositions may be used to treat cancers by methods such as inducing cellular necrosis and/or microvascular thrombosis, which can result in tumor regression.

Another aspect of the invention involves the use of biopolymer compositions to treat pleural effusions. Pleural effusions may be, for instance, ones that are refractory to medical therapy, such as malignant pleural effusions and benign, but recurrent, pleural effusions.

Another aspect of the invention involves the use of biopolymer compositions to seal bronchopleural fistulas. The compositions can be a foam or a gel. Bronchopleural fistulas may arise from, for example, airway leaks following surgery, lung trauma or invasive infection. The medical applications of the biopolymer compositions can be applied to the lung of a patient to seal airway leaks, by filling the airways and alveoli. The biopolymer compositions can be used to permanently seal the infected site of a patient, by forming a tissue-foam-tissue crosslink between a biopolymer and glutaraldehyde.

In certain embodiments, the present invention relates to a method of sealing a bronchopleural fistula in a patient, comprising the steps of administering a composition comprising a biopolymer, a cross-linker, and a polymeric additive; wherein said polymeric additive accelerates a cross-linking reaction between the biopolymer and the cross-linker, thereby sealing the fistula.

In certain embodiments, the composition is administered using a bronchoscope. In certain embodiments, the composition is administered using a catheter. In certain embodiments, the methods of the invention further comprise the step of advancing into a region of a lung of the patient via the trachea of the patient a catheter lumen through a bronchoscope.

Another aspect of the invention involves the use of biopolymer compositions to perform emergency tamponade of bleeding vessels. Examples of bleeding vessels include, but are not limited to, major internal limb vessels, gastrointestinal bleeding or internal organ bleeding. The biopolymer compositions may be used to treat bleeding vessels following trauma, surgery or gastrointestinal bleeding. The biopolymer compositions can be applied to permanently seal a bleeding vessel, by forming a tissue-foam-tissue crosslink between the biopolymer and glutaraldehyde which can act as a localized disinfectant. The biopolymer compositions can be applied to post surgical gastrointestinal bleeding thereby sealing the vessel and preventing ongoing blood loss.

Another aspect of the invention involves the use of biopolymer compositions to seal fistulas. Examples of fistulas include, but are not limited to, fistulas arising from gastrointestinal tumors and post surgical gastrointestinal fistulas. The biopolymer compositions may be used to seal fistulas in the gastrointestinal tract arising from tumors or surgery and thereby prevent fluid leakage into the surrounding site. The biopolymer compositions can be applied to permanently seal a gastrointestinal fistula, by forming a tissue-foam-tissue crosslink between the biopolymer and glutaraldehyde.

Another aspect of the invention involves the use of biopolymer compositions as a sealant to seal air leaks in a lung after surgery, for example.

Another aspect of the invention involves a method of attaching a first tissue to a second tissue of a patient in need thereof comprising, applying to said first tissue or said second tissue or both an effective amount of a composition comprising a biopolymer, a cross-linker, and a polymeric additive, thereby attaching said first tissue to said second tissue.

Another aspect of the invention involves the use of biopolymer compositions as a general topical hemostat. The biopolymer compositions can be used to control bleeding of, for example, a torn blood vessel. One embodiment of the invention relates to a method of achieving hemostasis, comprising applying to a blood vessel of a patient in need thereof a therapeutically effective amount of a composition comprising a biopolymer, a cross-linker, and a polymeric additive, thereby achieving hemostasis.

Another aspect of the invention involves the use of biopolymer compositions to achieve pleurodesis. The need for pleurodesis may arise from refractory medical therapy, such as malignant effusions and pleural space diseases. The biopolymer compositions can be used to fill the pleural space and thereby displace the recurrent effusions into the pleural space.

In certain embodiments, the present invention relates to a method of achieving pleurodesis in a patient, comprising the steps of administering a composition comprising a biopolymer, a cross-linker, and a polymeric additive; wherein said polymeric additive accelerates a cross-linking reaction between the biopolymer and the cross-linker. In certain embodiments, the composition is administered using a syringe. In certain embodiments, the composition is administered using a catheter.

EXEMPLIFICATION

The invention now being generally described, it will be more readily understood by reference to the following examples, which are included merely for purposes of illustration of certain aspects and embodiments of the present invention, and are not intended to limit the invention.

Example One

Bovine Serum Albumin & Glutaraldehyde In Vitro Experiments; Polymerization Time The following experiments were done to determine the effects of albumin and glutaraldehyde (GA) concentrations on polymerization time. In addition, the following experiments were done to determine the effects of additives (such as polyvinylpyrrolidone and dextran) on polymerization time of albumin/glutaraldehyde mixtures.

The following reagents and equipment were used: bovine serum albumin (Sigma A7906); polyvinylpyrrolidone (Aldrich 856568); glutaraldehyde 25% w/v (Acros 11998-0010); dextran HMW (Sigma D4876); water; 2 mL microfuge tubes; syringes; needles; timer; and a vortex mixer. The following stock solutions were prepared: a 45% albumin stock in water; a 50% PVP stock in water; and a 50% dextran stock in water.
B. General Procedure The general procedure used was that a glutaraldehyde mixture (0.1 mL) was added to an albumin mixture (0.9 mL), which may include polyvinylpyrrolidone or dextran, which was prepared in 2 mL microfuge tube. The combination was mixed for 5 seconds with Vortex. The microfuge tube inverted every 3 to 15 seconds. Polymerization time recorded when mixture no longer deforms visibly with inversion.

To measure the effects of albumin and glutaraldehyde (GA) concentrations on polymerization time, serial dilutions of albumin were combined with a fixed concentration of GA to assess the effects of albumin concentration on polymerization time. Albumin at concentrations from 13.5 to 36% was polymerized with 2% GA.

Serial dilutions of GA were combined with a fixed concentration of albumin to assess the effects of GA concentration on polymerization time. GA at concentrations from 0.25 to 2% GA was polymerized with 36% albumin.

Albumin and GA were combined at various ratios to assess the effects of albumin/GA ratio on polymerization time. Albumin at concentrations from 13.5 to 36% was combined with GA at concentrations from 0.25 to 2%, yielding Albumin/GA ratios from 6.75 to 144.

To measure the effects of polyvinylpyrrolidone (PVP) and dextran on polymerization time, PVP, over a range of concentrations, was added to albumin mixtures prior to polymerization with GA. For example, 25% albumin with 0 to 15% PVP was polymerized with GA 0.25 to 2%.

In addition, dextran, over a range of concentrations, was added to albumin mixtures prior to polymerization with GA to assess the effects on polymerization time. For example, 25% albumin with 0 to 15% dextran was polymerized with GA 0.25 to 2%.

Figure 2:
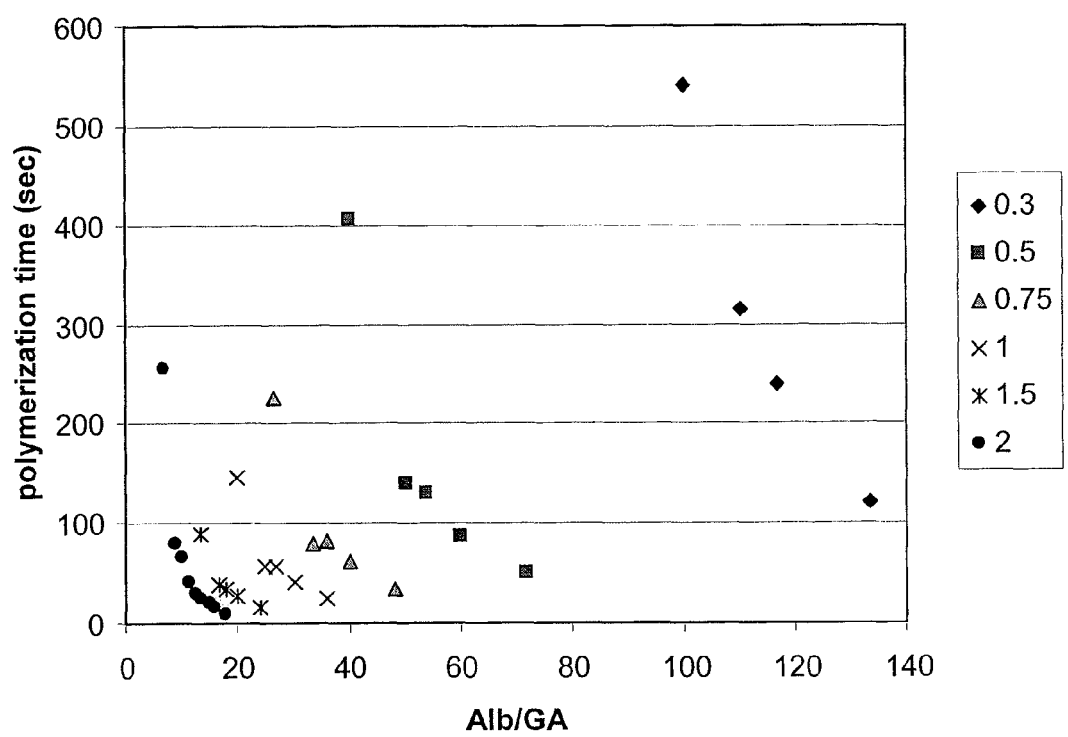
FIG. 2 depicts a graph showing the effects of albumin/glutaraldehyde ratio (Alb/GA) on polymerization time at room temperature. Each data set corresponds to a different glutaraldehyde concentration from 0.3 to 2%.

These experiments established that polymerization time varied inversely with albumin and GA concentrations and albumin/GA ratio. Polymerization times between 1 and 5 minutes could be achieved with albumin concentrations as low as 13.5% (with 2% GA) and GA concentrations as low as 0.25% (with 36% albumin). 36% albumin with 2% GA (Bioglue) polymerized in approximately 10 seconds. See FIGS. 1 and 2.

Figure 4:
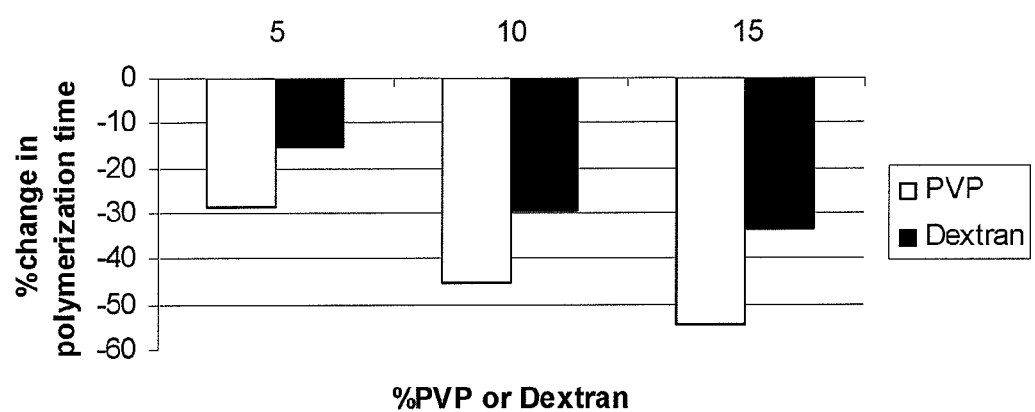
FIG. 4 depicts a bar graph comparing the results depicted in FIG. 3.

Addition of PVP shortened polymerization time 28.6 to 54.5% in a concentration dependent manner. Addition of dextran shortened polymerization time 15.4 to 33.7% in a concentration dependent manner. See FIGS. 3 and 4.

It can be concluded that albumin and glutaraldehyde can be mixed to create a tissue glue with polymerization time suitable for administration through a thin bore catheter for bronchoscopic lung volume reduction. In addition, addition of PVP or dextran shortens polymerization time such that lower concentrations of albumin and/or GA can be used. This effect may be used to improve the deliverability and/or biocompatibility of albumin/GA mixtures with appropriate polymerization characteristics. Further, the concentrations of albumin and GA in Bioglue® (36% albumin with 2% GA) result in polymerization time (approximately 10 seconds) well outside the ideal window for bronchoscopic lung volume reduction (approximately 1 to 5 minutes).

Example Two

Human Serum Albumin & Glutaraldehyde In Vitro Experiments; Polymerization Times The following experiments were done to determine the effect of substituting human serum albumin (HSA) for bovine serum albumin (BSA) on polymerization time of albumin/glutaraldehyde (GA) mixtures; and to determine if foams can be generated from such mixtures that can be injected through a small bore catheter.

The following reagents and equipment were used: 25% Human serum albumin (HSA; Baxter 1500233); polyvinylpyrrolidone (PVP; Aldrich 856568); glutaraldehyde 25% w/v (Acros 11998-0010); 2 mL microfuge tubes; syringes; needles; timer; vortex mixer; three-way stopcocks; and a 5F 130 cm single lumen catheter. The following stock solutions were prepared: 25% HSA with 5% PVP; and 25% HSA with 10% PVP.

In order to measure polymerization times, as described above, an albumin mixture (0.9 mL), which may include polyvinylpyrrolidone or dextran, was prepared in 2 mL microfuge tube. A glutaraldehyde mixture (0.1 mL) was then added. The combination was mixed for 5 seconds with Vortex. The microfuge tube inverted every 3 to 15 seconds. Polymerization time recorded when mixture no longer deforms visibly with inversion.

Serial dilutions of GA were combined with a fixed concentration of HSA to assess the effects of GA concentration on polymerization time. GA at concentrations from 0.25 to 0.5% GA was polymerized with 22.5% albumin (Note: all concentrations are listed as concentration after final mixing). The experiments were repeated with the addition of 4.5 or 9% PVP.

In order to measure foamability, an albumin mixture (4.5 mL) was drawn into syringe (30 mL) equipped with three-way stopcock attached. A glutaraldehyde mixture (0.5 mL) was then attached. Air (5-25 mL) was then drawn into second syringe (30 mL) and attached to sideport of three-way stopcock. Liquid and air were then mixed by alternately pushing the plungers of the two syringes (10-20 total pushes) to generate foam. Foam assessed for stability and homogeneity.

In order to measure injectability, an albumin mixture (4.5 mL) was drawn into syringe (20 mL) equipped with three-way stopcock attached. A glutaraldehyde mixture (0.5 mL) was then attached. Air (15 mL) was then drawn into second syringe (20 mL) and attached to sideport of three-way stopcock. Liquid and air were then mixed by alternately pushing the plungers of the two syringes (10-20 total pushes) to generate foam. The resulting foam was injected through 5F single-lumen catheter by hand. Time to inject and volume of injected foam recorded.

Figure 5:
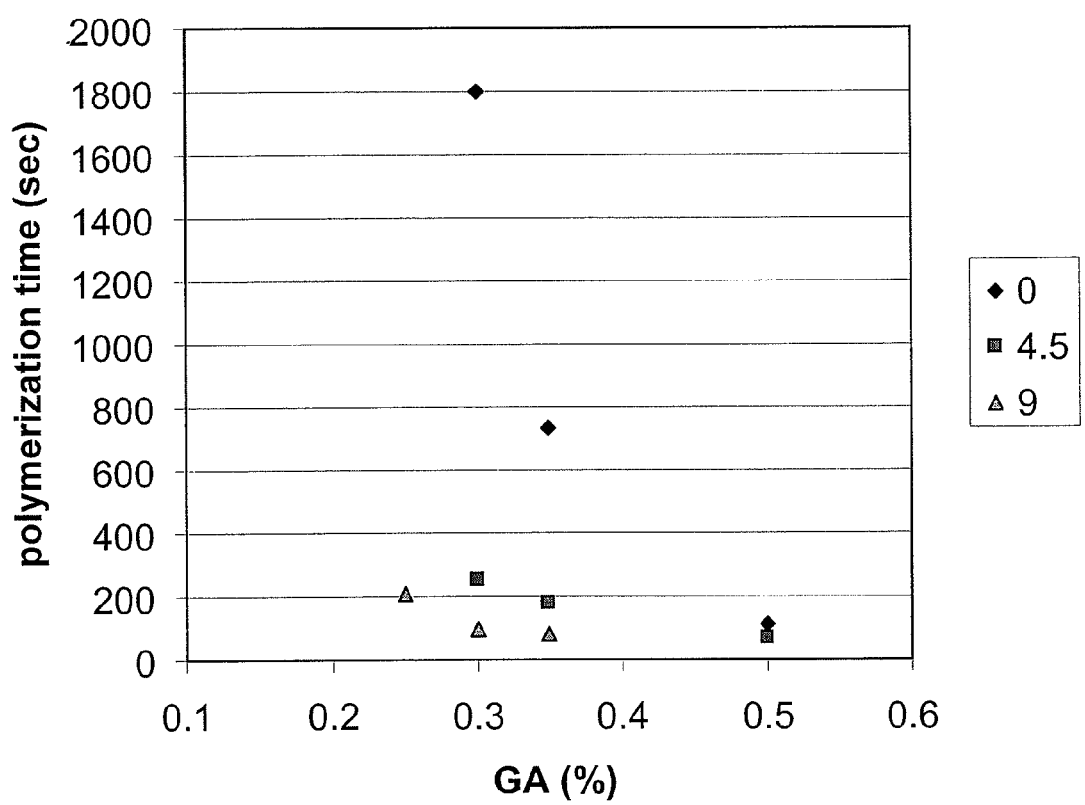
FIG. 5 depicts a graph showing the effects of glutaraldehyde (GA) concentration on polymerization time at room temperature. Each data set corresponds to a different polyvinylpyrrolidone (PVP) concentration from 0 to 9%.
Figure 6:
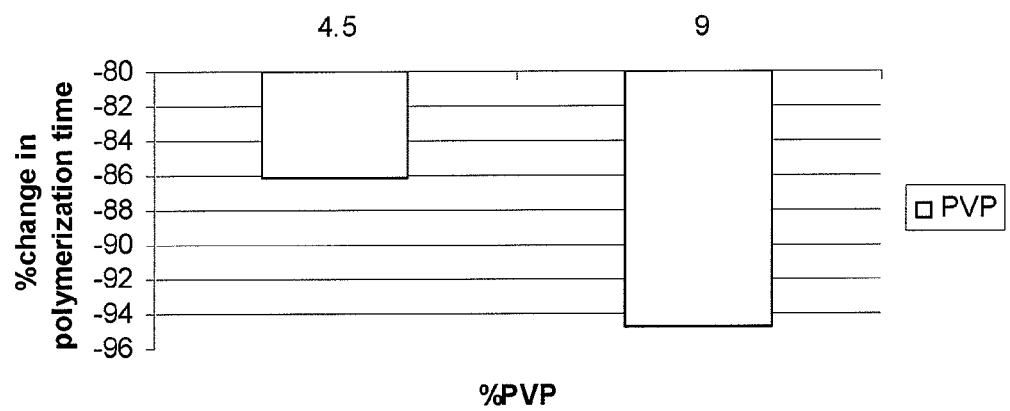
FIG. 6 depicts a bar graph comparing the effects of adding 4.5 or 9% polyvinylpyrrolidone (PVP) to a mixture of 22.5% human serum albumin (HSA) and 0.3% glutaraldehyde (GA) at room temperature.

These experiments established that polymerization time varies inversely with GA concentration. Interestingly, HSA appeared to polymerize more quickly than BSA at similar concentrations. Further, addition of PVP significantly shortened polymerization time. The magnitude off the affect seemed to be larger that seen with BSA under similar conditions. For example, at Liquid:Air ratios of 1:3 or less, 22.5% HSA with 4.5% PVP formed a stable and injectable foam. See FIGS. 5 and 6, as well as Tables 1 and 2 (in FIG. 7).

It can therefore be concluded that HSA can be substituted for BSA in albumin/GA mixtures designed for administration through a thin bore catheter for bronchoscopic lung volume reduction. In addition, addition of PVP has been shown to shorten polymerization time. Finally, 22.5% HSA with 4.5% PVP and 0.3% GA can be mixed with air at a 1:3 ratio to form a foam stable enough to inject through a small bore catheter.

Example Three

Albumin/GA In Vivo Experiments in Sheep

As disclosed in the previous examples, albumin/GA mixtures with desirable properties for BLVR were identified through a series of in vitro experiments. In this example, these formulations were used to perform BLVR in sheep to evaluate efficacy and toxicity of these formulations.

Anesthesia was induced with ketamine 2 mg/kg, midazolam 0.3 mg/kg, and propofol 70 mg IV and maintained with propofol continuous infusion. Animals were intubated fiberoptically with a 10 mm oral endotracheal tube and mechanically ventilated with RR 12, TV 500. A baseline CT scan was obtained at 25 cm H2O transpulmonary pressure, measured with an esophageal balloon.

The bronchoscope was wedged in a target segmental airway. The delivery catheter was passed through the working channel of the bronchoscope until its tip was visible 1-2 cm beyond the end of the bronchoscope.

The GA solution was added to the albumin solution and mixed with oxygen from a wall source. A foam was generated by pushing the liquid and gas repeatedly through two syringes connected by a three-way stopcock. The foam was drawn into one of the syringes which was attached to the proximal end of the catheter and injected by hand. The whole mixing and injection procedure took place within approx. 1 minute. The catheter was then removed and air was injected through the working channel to push the foam distal. After 2-3 minutes, the bronchoscope was removed from wedge position and the site was inspected for evidence of proper polymerization of the foam.

The bronchoscope was then wedged at the next target segment where the procedure was repeated. Following completion of the last treatment, a repeat CT scan was obtained at 25 cm H2O transpulmonary pressure.

In recovery, anesthesia was discontinued and the animal was extubated and allowed to recover. All sheep were treated with 4 days of broad-spectrum antibiotics (Baytril) beginning immediately prior to BLVR. Repeat CT scans were performed at selected timepoints prior to euthanasia/necropsy. Specifically, six to eight-five days following BLVR, repeat CT scans were performed at 25 cm $H_2O$ transpulmonary pressure. The animals were then euthanized and necropsied. The abdominal and thoracic organs were inspected. The lungs were removed enbloc and inflated and the treatment sites were evaluated semiquantitatively on a scale of 0 to 3 for their size and contraction. The sites were then dissected and evaluated for evidence of hemorrhage, necrosis, or other gross evidence of toxicity. Tissue samples were taken from each lung treatment site as well as untreated control sites and preserved in 10% buffered formalin for later histologic processing. Samples of heart, liver, kidney, and spleen were also collected and processed in similar fashion.

In order to measure the effects of albumin and glutaraldehyde concentrations in vivo, five sheep were treated with five formulations containing a range of BSA concentrations from 20 to 38% and GA concentrations from 0.25 to 0.75%. The animals were followed for 8-9 days. See Table 3 (FIG. 7).

CT scans immediately post-BLVR revealed a combination of hazy infiltrates and denser, more linear infiltrates in all animals. CT scans at one week revealed progression towards denser, more linear infiltrates. Volume reduction of 22.5 to 76.9 mL per site treated was detected by CT integration post treatment. Results at one week were more variable. Other CT findings at one week included cavities at treatment sites in sheep 269b, 274, and 256, and pneumomediastinum and pneumothorax in sheep 266. In most cases, the cavities were also visible on post-treatment CTs.

There was no gross evidence of heart, kidney, liver, or spleen toxicity in any animal. There were no pleural adhesions in any animal. Treatment sites were easily identified and well localized. Size and contraction scores ranged from 2.13 to 2.88 out a possible 3. The percentage of sites with hemorrhage/necrosis ranged from 12.5 to 87.5% and was highest in the two groups with the highest GA concentrations. Cavities at treatment sites were identified in animals 269b, 274, 266, and 256.

It can therefore be concluded that the albumin/GA mixtures tested were effective in producing bronchoscopic lung volume reduction. In addition, albumin/GA mixtures with higher GA were associated with fevers during the first 3 days post treatment. Further, albumin/GA mixtures with higher GA cause excessive local lung toxicity in the form of hemorrhage/necrosis. Finally, the albumin/GA mixtures tested sometimes produce cavities at treatment sites which appear to be immediate mechanical complications of the procedure.

Importantly, attempts to balance polymerization time and toxicity due to higher glutaraldehyde concentration did not produce a clinically workable solution as on one hand, higher albumin concentration with lower glutaraldehyde led to long polymerization times and to very viscous solutions which very essentially impossible to inject through a narrow bore catheter, while on the other hand lower albumin concentrations with higher glutaraldehyde concentrations led to marked toxicity.

The first set of experiments (described above) indicated that the approach chosen seemed to induce lung volume reduction; however, to achieve a reasonable operating time, the glutaraldehyde concentration had to be relatively high. This was associated with necrosis and hemorrhage at the treatment sites. Therefore, in the next set of experiment, the mixture included the polymeric additive, PVP, shown to accelerate the polymerization of albumin/glutaraldehyde mixtures.

In order to measure the effects of PVP in vivo, eight animals were treated with a formulation containing 25% BSA, 10% PVP, and 0.25% GA. All animals were treated at a total of eight sites with 4 on each lung). One animal (sheep 143) was treated with 5 mL of the albumin/PVP/GA mixture mixed with 5 mL of oxygen to generate 10 mL of foam. The remaining animals were treated with 5 mL of the albumin/PVP/GA mixture mixed with 15 mL of oxygen to generate 20 mL of foam. See Table 4 (FIG. 8).

It was found that no sheep developed fevers (T>103.5) during the first three days following BLVR. Sheep 143 and 4 developed cough increased respiratory effort. No animal required additional treatments. All animals survived to planned euthanasia/necropsy. CT scans immediately post-BLVR revealed a combination of hazy infiltrates and denser, more linear infiltrates in all animals. CT scans at one week revealed progression towards denser, more linear infiltrates. Subsequent CT scans showed persistence of these findings. Volume reduction of 12.6 to 185.9 mL per site treated was detected by CT integration at one week. Sheep 143 had pneumomediastinum and a pneumothorax as well as a cavity at a treatment site on one week CT scan.

There was no gross evidence of heart, kidney, liver, or spleen toxicity in any animal. There were no pleural adhesions in any animal. Treatment sites were easily identified and well localized. Size and contraction scores ranged from 1.88 to 2.75 out a possible 3. There was no gross hemorrhage/necrosis in any animal. Sheep 143 had a cavity at one treatment site.

Therefore it can be concluded that 25% BSA, 10% PVP, 0.25% GA produces effective bronchoscopic volume reduction. Importantly, there were no fevers and no gross evidence of excessive local pulmonary or systemic toxicity associated with this formulation. Finally, there were fewer mechanical complications (cavities at treatment sites) associated with this formulation compared with previously tested BSA/GA mixtures without PVP.

In order to measure the effects of replacing BSA with HSA, four animals were treated with a formulation containing 22.5% HSA, 4.5% PVP, and 0.3% GA. One animal was treated with 5 mL of the albumin/PVP/GA mixture mixed with 15 mL of oxygen to generate 20 mL of foam. One animal was treated with 10 mL of the albumin/PVP/GA mixture mixed with 20 mL of oxygen to generate 30 mL of foam. See Table 5 (FIG. 8).

It was found that no sheep developed fevers (T>103.5) during the first three days following LVR. Both animals survived to planned euthanasia/necropsy. CT scans immediately post-LVR revealed a combination of hazy infiltrates and denser, more linear infiltrates in all animals. CT scans at one week revealed progression towards denser, more linear infiltrates. Volume reduction of 19.6 to 81.2 mL per site treated was detected by CT integration at one week. There were no other CT abnormalities.

Importantly, there was no gross evidence of heart, kidney, liver, or spleen toxicity in any animal. There were no pleural adhesions in any animal. Treatment sites were easily identified and well localized. Size and contraction scores ranged from 2.25 to 3 out a possible 3. There was gross evidence of a small amount of hemorrhage/necrosis at one site in animal 308. There were no cavities at treatment sites in any animal. See Table 6 (FIG. 8).

In can therefore be concluded that a composition of 22.5% HSA, 4.5% PVP, 0.3% GA produces effect bronchoscopic volume reduction. Remarkably, there were no fevers associated with this treatment. Finally, the small amount of hemorrhage/necrosis seen at one treatment site in one sheep did not appear to be clinically significant.

Example Four

Long-Term Lung Volume Reduction Treatment in Healthy Sheep

The following formulation was tested in-vivo in 4 healthy, female sheep: 25% BSA, 6% PVP, 0.25% GA

TABLE 1

| Treatment groups | | | |
|---|---|---|---|
| Sheep | Group | Sites | Days from treatment to necropsy |
| 652 | BSA/PVP | 6 | 92 |
| 659 | | 6 | 92 |
| 602 | | 6 | 90 |
| 605 | | 6 | 90 |

Anesthesia was induced with ketamine 2 mg/kg, midazolam 0.3 mg/kg, and propofol 70 mg IV and maintained with propofol continuous infusion. Animals were intubated fiberoptically with a 10 mm oral endotracheal tube and mechanically ventilated with RR 12, TV 500. A baseline CT scan was obtained at 25 cm $H_2O$ transpulmonary pressure, measured with an esophageal balloon.

Simultaneous recordings of flow and transpulmonary pressure were collected during tidal breathing using a pneumotach and pressure transducer and WinDaq data acquisition system. The same setup was used to collect pressure and volume data during stepwise deflation from transpulmonary pressure ≥30 to FRC.

The bronchoscope was wedged in a target segmental airway. The delivery catheter was passed through the working channel of the bronchoscope until its tip was visible 1-2 cm beyond the end of the bronchoscope. The GA solution was added to the Albumin/PVP solution and mixed with oxygen from a wall source. Foam was generated by pushing the liquid and gas repeatedly through two syringes connected by a three-way stopcock. The foam was drawn into one of the syringes, which was attached to the proximal end of the catheter and injected by hand. The catheter was then removed and air was injected through the working channel to push the foam distal. After 2-3 minutes, the bronchoscope was removed from wedge position and the site was inspected for evidence of proper polymerization of the foam. The bronchoscope was then wedged at the next target segment where the procedure was repeated. Five mL of liquid was combined with 15 mL of 100% $O_2$ yielding 20 mL of foam at each treatment site. 6 sites were treated in the caudal and middle lobes of each sheep, depending on the size of the sheep. Sites were distributed between dorsal and lateral sites. Following completion of the last treatment, a repeat CT scan was obtained at 25 cm $H_2O$ transpulmonary pressure. Physiology measurements were also repeated.

In recovery, anesthesia was discontinued and the animal was extubated and allowed to recover. All sheep were treated with 4 days of broad-spectrum antibiotics (Baytril) beginning immediately prior to treatment. Repeat CT scans and physiology were performed at 1, 4, 8, and 12 weeks. At 12 weeks following treatment, repeat CT scans were performed at 25 cm $H_2O$ transpulmonary pressure. The animals were then euthanized and necropsied. The abdominal and thoracic organs were inspected. The lungs were removed enbloc and inflated and the treatment sites were evaluated semiquantitatively on a scale of 0 to 3 for their size and contraction. The sites were then dissected and evaluated for evidence of hemorrhage, necrosis, or other gross evidence of toxicity. Tissue samples were taken from each lung treatment site as well as untreated control sites and preserved in 10% buffered formalin for later histologic processing. Samples of heart, liver, kidney, and spleen were also collected and processed in similar fashion.

Figure 9:
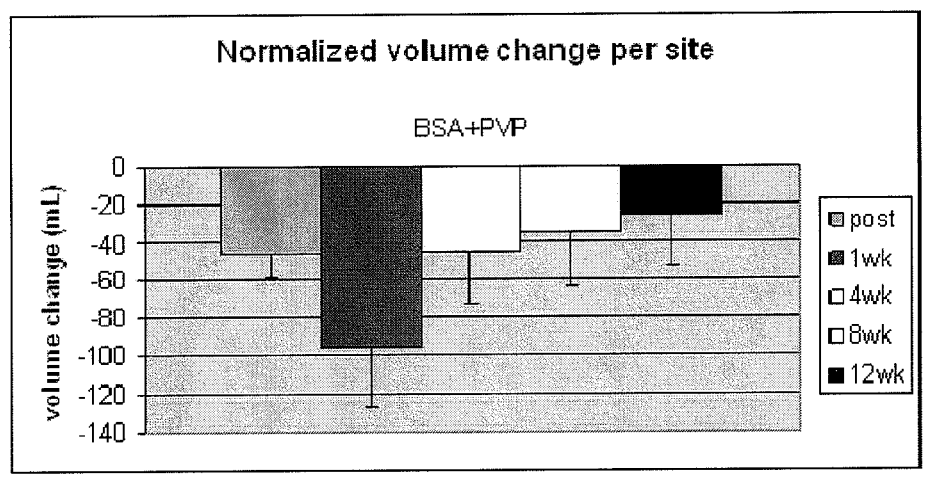
FIG. 9 depicts a graph showing results of lung volume reduction study in sheep using a mixture of 25% BSA, 6% PVP and 0.25% GA.

Based on our clinical findings, the sheep used in the experiment generally tolerated the lung volume reduction procedure well. CT scans were analyzed quantitatively using the Emphylxj software. Changes in total volume, right side (treated) volume, and right side normalized to left side (to account for differences in inflation pressure) were divided by the number of sites treated to yield volume changes per site. The results are shown in FIG. 9. Flow data were integrated to yield volume and corrected for drift. Resistance (R) and compliance (C) were calculated by the covariance method using a Matlab program. Pressure volume curves were generated from the step-wise deflation data and fit to the equation of Salazar and Knowles to yield Vmax, A, k, and Vmin using a separate Matlab program. There were no physiological changes in Vmax and A between baseline and 12 weeks.

Incorporation By Reference

All of the U.S. patents and U.S. published patent applications cited herein are hereby incorporated by reference.

Equivalents

While several embodiments of the present invention are described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:

1. A method for reducing lung volume in a patient, comprising the steps of
    a) inserting a bronchoscope through the trachea of a patient in need thereof to reach a lung segment to be treated; wherein said bronchoscope comprises a working channel;
    b) inserting a catheter through said working channel; and
    c) administering through the catheter to the lung segment a therapeutically effective amount of a composition comprising a biopolymer, a cross-linker, and a polymeric additive;
    wherein
    said polymeric additive accelerates a cross-linking reaction between the biopolymer and the cross-linker;
    the composition is administered in an amount sufficient to reduce lung volume, but without systemic toxicity; and
    i) the biopolymer is bovine serum albumin in about 25% by weight of the composition; the cross-linker is glutaraldehyde in about 0.25% by weight of the composition; and the polymeric additive is poly(vinylpyrrolidone) in about 10% by weight of the composition; or
    ii) the biopolymer is human serum albumin in about 22.5% by weight of the composition; the cross-linker is glutaraldehyde in about 0.3% by weight of the composition; and the polymeric additive is poly(vinylpyrrolidone) in about 4.5% by weight of the composition.

2. The method of claim 1, wherein the composition is a foam or a gel.

* * * * *